United States Patent [19]
Klein

[11] Patent Number: 5,863,284
[45] Date of Patent: Jan. 26, 1999

[54] DEVICES AND METHODS FOR RADIATION TREATMENT OF AN INTERNAL BODY ORGAN

[75] Inventor: Enrique J. Klein, Los Altos, Calif.

[73] Assignee: Localmed, Inc., Palo Alto, Calif.

[21] Appl. No.: 697,190

[22] Filed: Aug. 20, 1996

Related U.S. Application Data

[63] Continuation-in-part of Ser. No. 555,457, Nov. 13, 1995.

[51] Int. Cl.$^6$ ........................................................ A61N 5/00
[52] U.S. Cl. ......................................................... 600/3
[58] Field of Search ............................................. 600/1–8

[56] References Cited

U.S. PATENT DOCUMENTS

| | | |
|---|---|---|
| 3,324,847 | 6/1967 | Zoumboulis . |
| 3,811,426 | 5/1974 | Culver et al. . |
| 4,323,055 | 4/1982 | Kubiatowicz . |
| 4,581,017 | 4/1986 | Sahota . |
| 4,584,991 | 4/1986 | Tokita et al. . |
| 4,706,652 | 11/1987 | Horowitz ................................ 600/8 |
| 4,768,507 | 9/1988 | Fischell et al. . |
| 4,790,315 | 12/1988 | Mueller, Jr. et al. . |
| 4,796,629 | 1/1989 | Grayzel . |
| 5,053,033 | 10/1991 | Clarke . |
| 5,059,166 | 10/1991 | Fischell et al. . |
| 5,199,939 | 4/1993 | Dake et al. . |
| 5,213,561 | 5/1993 | Weinstein et al. . |
| 5,302,168 | 4/1994 | Hess . |
| 5,308,356 | 5/1994 | Blackshear, Jr. et al. .............. 606/194 |
| 5,336,178 | 8/1994 | Kaplan et al. . |
| 5,344,402 | 9/1994 | Crocker . |
| 5,411,466 | 5/1995 | Hess . |
| 5,484,384 | 1/1996 | Fearnot . |
| 5,503,613 | 4/1996 | Weinberger . |
| 5,522,961 | 6/1996 | Leonhardt . |
| 5,616,114 | 4/1997 | Thornton et al. ........................... 600/3 |
| 5,662,580 | 9/1997 | Bradshaw et al. .......................... 600/3 |

FOREIGN PATENT DOCUMENTS

| | | |
|---|---|---|
| 0 539 136 A1 | 4/1994 | European Pat. Off. . |
| WO 96/22121 | 7/1996 | Germany . |
| WO 94/26205 | 11/1994 | WIPO . |
| WO 95/19807 | 7/1995 | WIPO . |

OTHER PUBLICATIONS

Wiedermann et al., "Intracoronary Irradiation Markedly Reduces Restenosis After Balloon Angioplasty in a Porcine Model.", 1993, Supplement to *Circulation*, vol. 88, No. 4, pt. 2, p. I–655, *Abstract No. 3529.

Wiedermann et al., "Intracoronary Irradiation Acutely Impairs Endothelial and Smooth Muscle Function as Assessed by Intravascular Ultrasound.", 1992, Supplement to *Circulation*, vol. 86, No. 4, p. I–188, *Abstract No. 0750.

Popowski et al. "High Dose Rate Brachytherapy for Prevention of Restenosis After Percutaneous Transluminal Coronary Angioplasty: Preliminary Dosimetric Tests of a New Source Presentation", 1995, *Int. J. Radiation Oncology Biol. Phys.*, vol. 33, No. 1, pp. 211–215.

(List continued on next page.)

*Primary Examiner*—John P. Lacyk
*Attorney, Agent, or Firm*—Townsend and Townsend and Crew LLP

[57] ABSTRACT

The invention provides methods and devices for delivering low level radiation to inhibit neointimal hyperplasia following angioplasty or other intravascular procedures. In an exemplary method, a balloon is inflated within a stenosed region of a blood vessel to produce a treated region. The balloon is then deflated and a radioactive source within a sleeve is aligned over the deflated balloon. The balloon is again inflated at the treated region to engage the sleeve having the radioactive source against the blood vessel within the treated region for from 1 to 40 minutes to deliver a sufficient dose of radiation to inhibit neointimal hyperplasia.

122 Claims, 24 Drawing Sheets

OTHER PUBLICATIONS

Verin et al., "Intra–arterial Beta Irradiation Prevents Neointimal Hyperplasia in a Hypercholesterolemic Rabbit Restenosis Model.", 1995, *J. Amer. College of Cardiology*, *Abstract No. 407–6.

Verin et al., "Intra–arterial Beta Irradiation Prevents Neointimal Hyperplasia in a Hypercholesterolemic Rabbit Restenosis Model.", 1995, *Circulation*, vol. 92, No. 8, pp. 2284–2290.

Waksman et al., "Intracoronary Radiation Before Stent Implantation Inhibits Neointima Formation in Stented Porcine Coronary Arteries", 1995, *Circulation*, vol. 92, No. 6, pp. 1383–1386.

Waksman et al., "Endovascular Low–Dose Irradiation Inhibits Neointima Formation After Coronary Artery Balloon Injury in Swine", 1995, *Circulation*, vol. 91, No. 5, pp. 1533–1539.

Wiedermann et al., "Intracoronary Irradiation Markedly Reduces Restenosis After Balloon Angioplasty in a Porcine Model.", 1994, *J. American College of Cardiology*, vol. 23, No. 6, pp. 1491–1497.

Wiedermann et al., Intracoronary Irradiation Markedly Reduces Neointimal Proliferation After Balloon Angioplasty in Swine: Persistent Benefit at 6–Month Follow–Up.: 1995, *J. American College of Cardiology*, vol. 25, No. 6, pp. 1451–1456.

Hehrlein et al., "Low–Dose Radioactive Endovascular Stents Prevent Smooth Muscle Cell Proliferation and Neointimal Hyperplasia in Rabbits", 1995, *Circulation*, vol. 92, pp. 1570–1575.

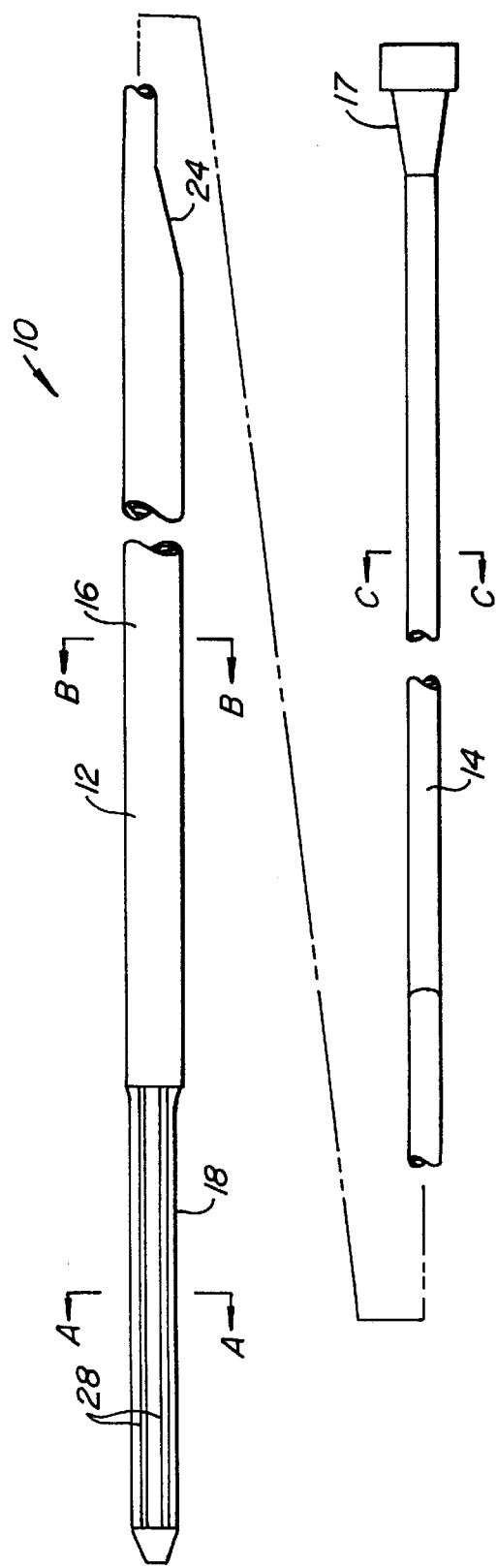
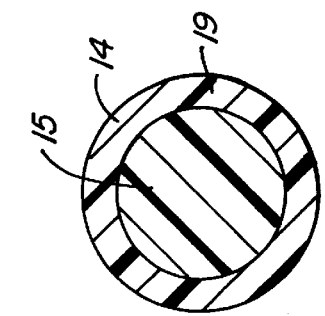
FIG. 1.
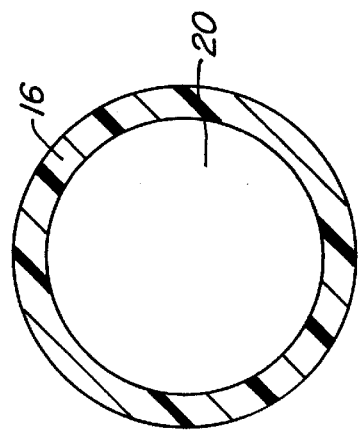
FIG. 1B.
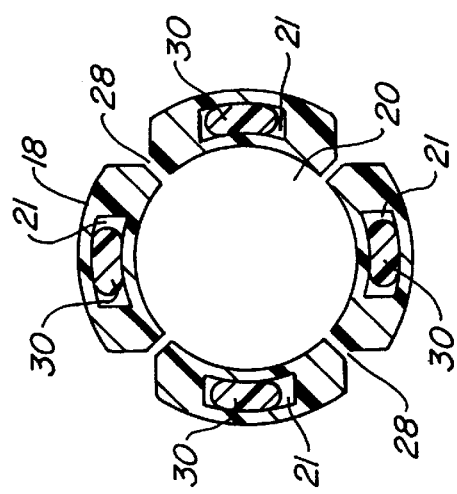
FIG. 1A.

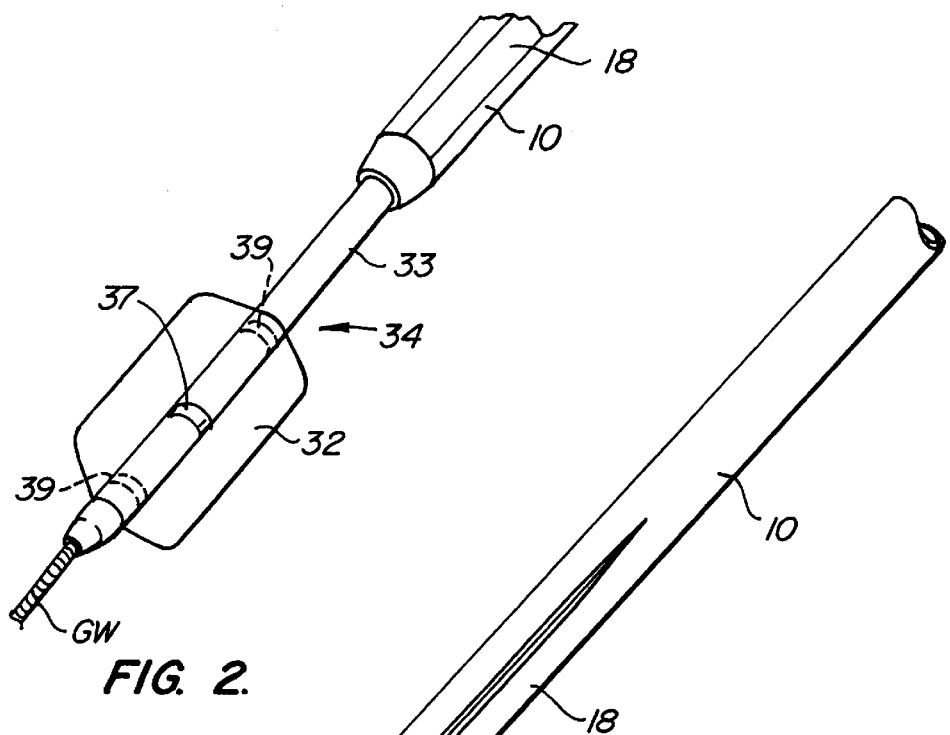
FIG. 2.
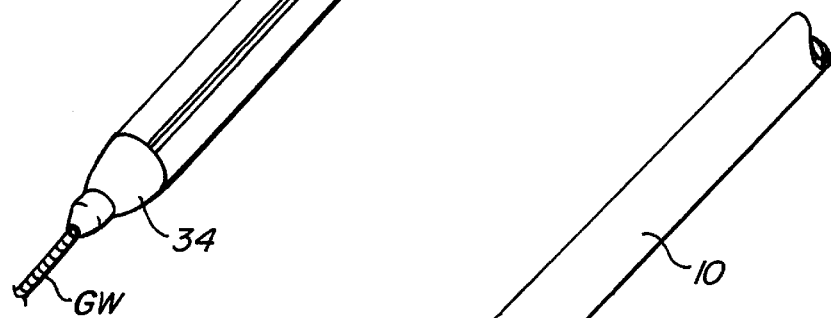
FIG. 3.
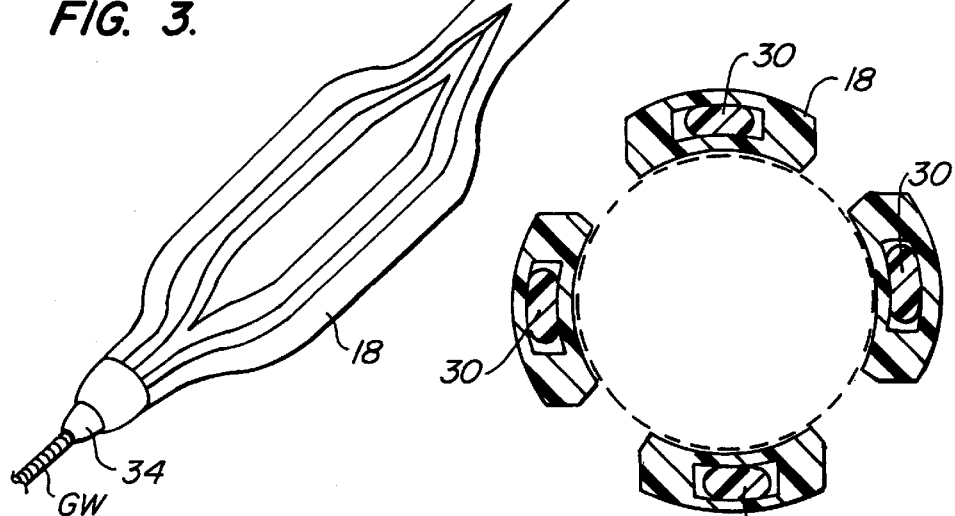
FIG. 4.
FIG. 4A.

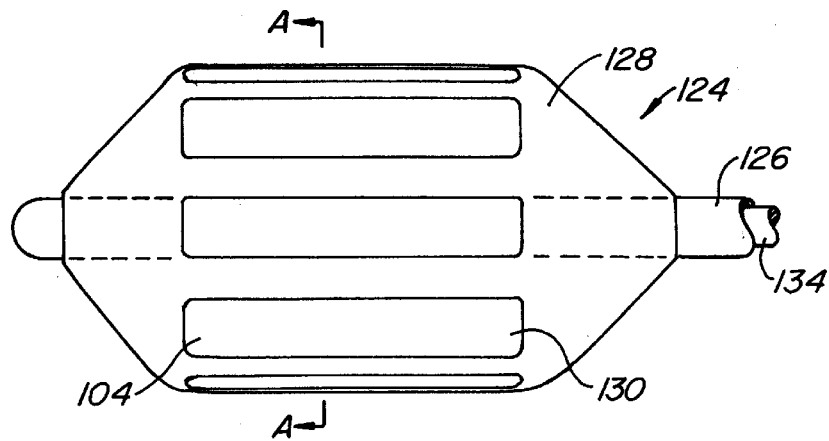
FIG. 22.
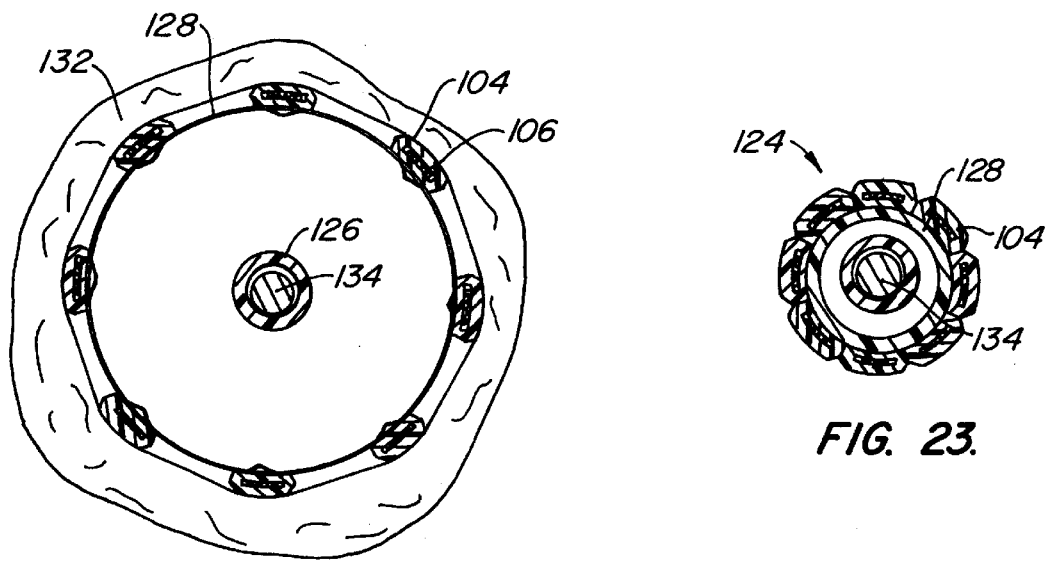
FIG. 22A.
FIG. 23.

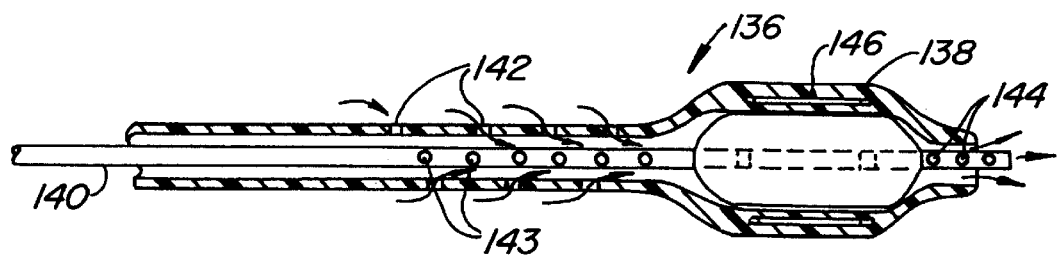
FIG. 24.
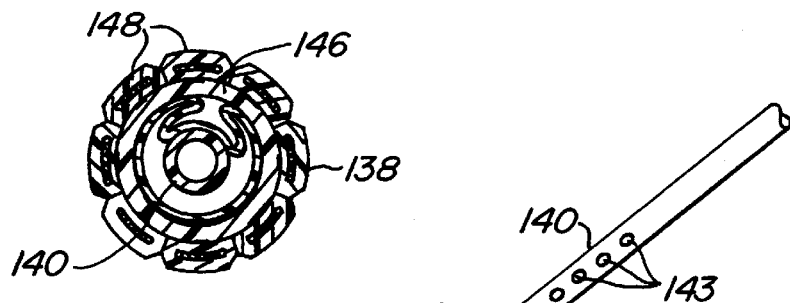
FIG. 25.
FIG. 26.
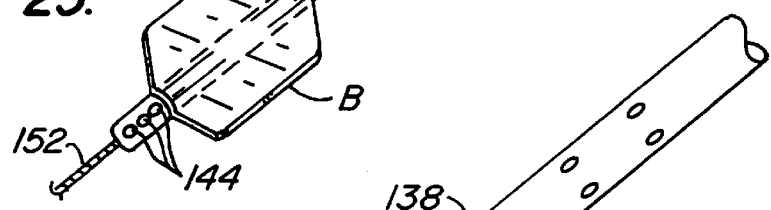
FIG. 27.
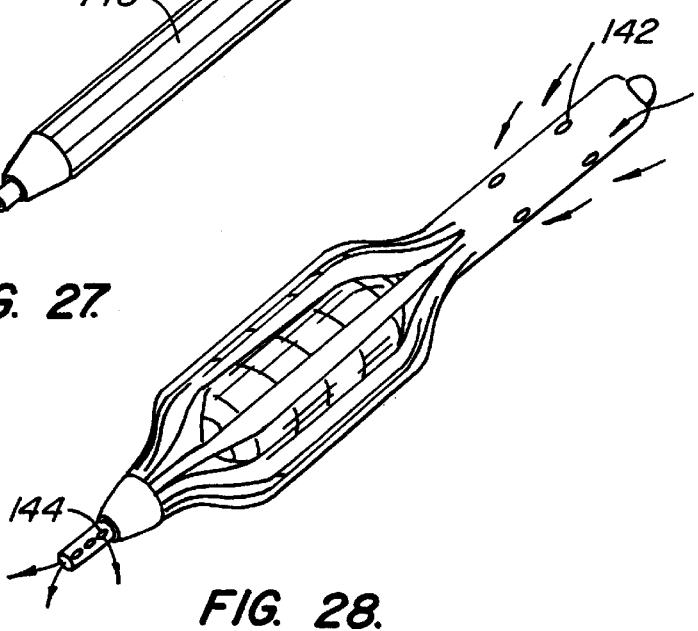
FIG. 28.

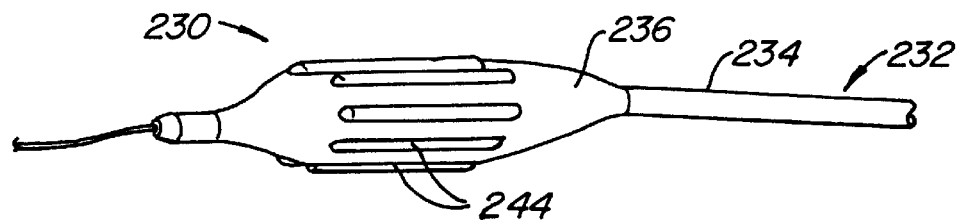
FIG. 44.
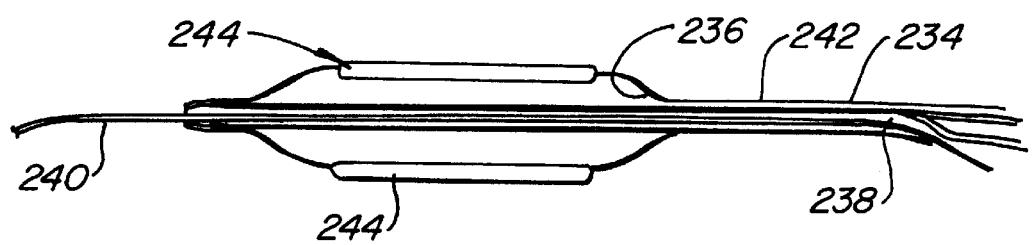
FIG. 45.
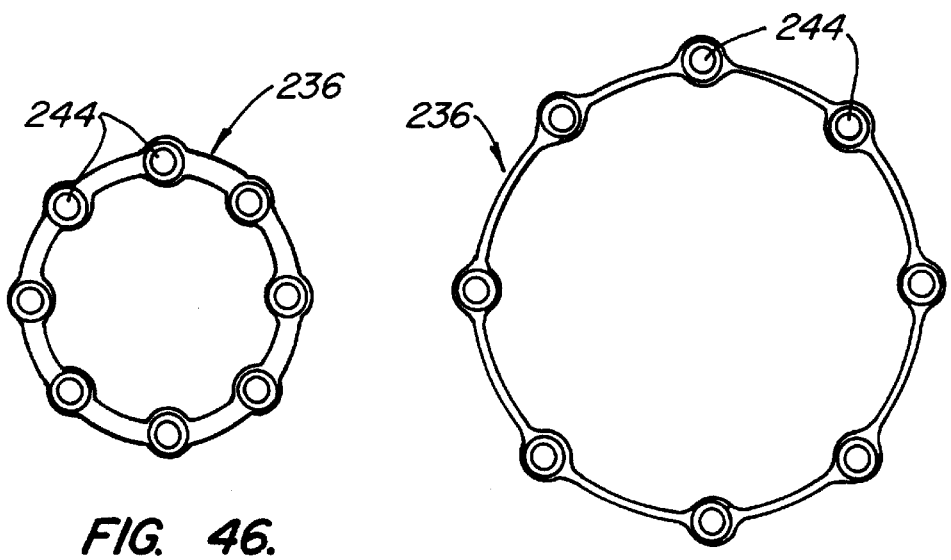
FIG. 46.
FIG. 47.

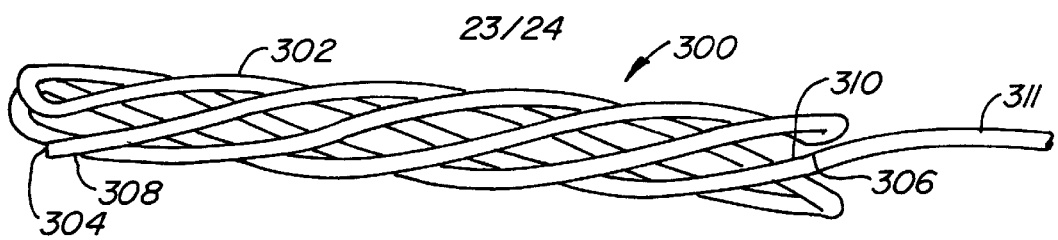
FIG. 53.
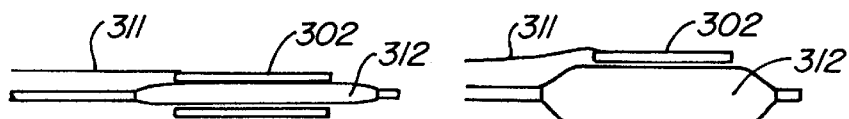
FIG. 54A.      FIG. 54B.
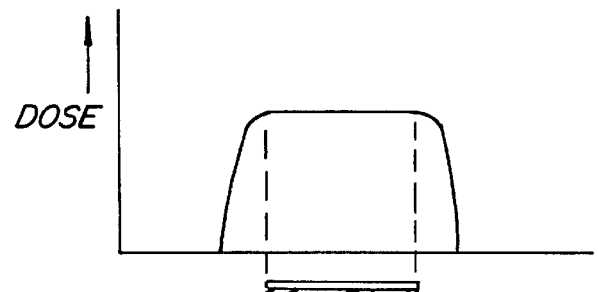
FIG. 55.
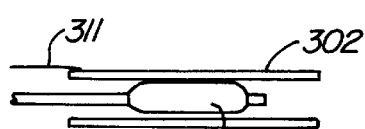   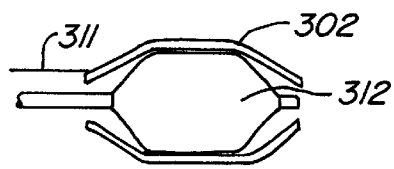
FIG. 56A.      FIG. 56B.
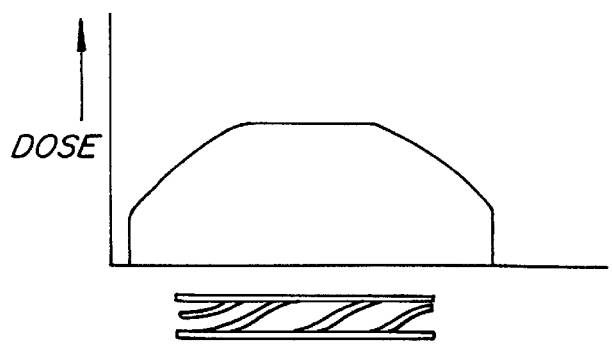
FIG. 57.

DEVICES AND METHODS FOR RADIATION TREATMENT OF AN INTERNAL BODY ORGAN

CROSS REFERENCE TO RELATED APPLICATIONS

This application is a continuation in part application of U.S. patent application Ser. No. 08/555,457, filed Nov. 13, 1995, the complete disclosure of which is herein incorporated by reference.

BACKGROUND OF THE INVENTION

This invention relates generally to the treatment of diseased arteries. More specifically, the invention provides for the internal irradiation of a blood vessel preceding or following an angioplasty or atherectomy procedure, or the implantation of a stent.

Percutaneous transluminal angioplasty is an exemplary procedure in treating peripheral vessels or the coronary vessels surrounding the heart. During angioplasty, a catheter having an expansible distal end, usually in the form of a balloon, is positioned in a lumen of a blood vessel with the distal end disposed within a stenotic atherosclerotic region of the vessel. The expansible end is then expanded to dilate the vessel and restore adequate blood flow through the diseased region.

While angioplasty has gained wide acceptance, it continues to be limited by two major problems, abrupt closure and restenosis. Abrupt closure refers to the acute occlusion of a vessel immediately after or within the initial hours or days following the dilation procedure. This complication, occurring in approximately one in twenty cases, may result in myocardial infarction and death if blood flow is not quickly restored.

Restenosis refers to the re-narrowing of an artery after a successful angioplasty procedure. Restenosis usually occurs within the initial six months after angioplasty and afflicts approximately one in every two or three cases. Therefore, over one-third of treated patients will require additional revascularization procedures. Many different strategies have been tried to reduce the restenosis rate with mixed results, including mechanical (e.g., prolonged balloon inflations, atherectomy, laser and stenting) and pharmacologic (e.g., calcium antagonists, ace inhibitors, fish oils and steroids) approaches.

One promising new strategy for preventing restenosis is to irradiate the treated section of the coronary artery. Such procedures have been proposed in the past by placing a radiation-emitting source in the coronary artery before or after dilatation. Several of such irradiation procedures are described in, for example, U.S. Pat. Nos. 5,059,166, 5,199,939 and 5,302,168 and PCT Application WO 95/19807. Although a variety of procedures have been proposed for irradiating a treated vessel region, most of such procedures lack the ability to conveniently and safely introduce a radiation source into a treated vessel region, to distribute the radiation source(s) uniformly within the treated vessel region, or to provide the best suited type of radiation to the vessel of the lowest activation level, preferably over a short period of time.

For these and other reasons it would be desirable to provide methods and apparatus which would reduce or greatly eliminate such drawbacks. Such methods and devices should allow for the easy and rapid introduction and withdrawal of the radioactive source and provide for the rapid and uniform irradiation of the treated vessel region.

SUMMARY OF THE INVENTION

The invention provides devices and methods for performing angioplasty, and more particularly for internally irradiating a treated vessel region following balloon dilatation with an angioplasty balloon catheter. To internally irradiate the vessel, the invention employs various schemes to place one or more radioactive sources in apposition with a vessel wall following angioplasty. The radioactive source(s) are preferably positioned such that they will be evenly circumferentially spaced within the vessel and longitudinally aligned with the treated region so as to produce a generally uniform radiation dose distribution at the vessel wall.

To place the radioactive sources in apposition with the vessel wall in a desired pattern or distribution, the invention employs a radially expansible member. Exemplary radially expansible members include non-compliant balloons, e.g., a conventional angioplasty balloon, elastomeric balloons, and the like. Further, the radioactive sources may be self supporting, directly attached to the balloon (hereinafter "balloon attachment") or attached to a sleeve which is slidably disposed over the balloon (hereinafter "sleeve attachment").

The radioactive sources will preferably emit gamma ($\gamma$) or beta ($\beta$) radiation, with the preferred being $\beta$ radiation. Exemplary of $\beta$-emitting sources include $^{90}$Strontium and $^{90}$Yttrium. Exemplary $\beta$-emitting sources include $^{125}$Iodine and $^{192}$Iridium which emits both $\gamma$ and $\beta$ radiation. Preferred is use of $^{90}$Strontium in secular equilibrium with $^{90}$Yttrium as a $\beta$-emitter. The radioactive sources will preferably comprise a plurality of discrete elements, such as, for example, seeds, elongate strips, ribbons, wires, ribs, and the like.

A preferred configuration of a radioactive source is a seed which includes a housing and radionuclides which are contained within an axial lumen of the housing. The housing is preferably very flexible in the transverse direction so that it may adequately traverse the tortuous path through a patient's vasculature. The housing is preferably constructed of a material displaying resilient properties, such as a radiation resistant polymer reinforced with a flexible stainless steel braiding or a superelastic nickel titanium housing. Containing the radionuclides within a housing is further advantageous in that the seeds may be reused. In one exemplary embodiment, the seed is folded into an expansible cage structure which may be expanded by a balloon. In this manner, a single reusable seed is employed to provide an even circumferential radiation dose distribution.

Each seed will usually include at least one open end into which the radionuclides may be placed. End caps will preferably be provided which may be inserted into each open end to seal the radionuclides within the housing. The end caps may be constructed of a non-metallic material such as cyanoacrylate, epoxy, and the like. Alternatively, the end caps may be constructed of a metallic material such as stainless steel or nickel titanium, and will typically be attached to the housings by brazing, welding, crimping and/or with the use of adhesives such as cyanoacrylate or epoxy. Further, the end caps may be constructed of a radiopaque material, such as nickel titanium, gold, tungsten, platinum, or tantalum, so that the end caps may serve as fluoroscopic markers.

The radionuclides will preferably be spherical in geometry and will be constructed of a ceramic like material containing $^{90}$Strontium and $^{90}$Yttrium. In this manner, the seeds will be configured to emit pure beta radiation to a treatment site.

To provide a more uniform circumferential radiation dose distribution at the vessel wall, the invention provides various configurations of energy attenuators that are used in combination with the radioactive sources. The attenuators are placed between the radioactive sources and the vessel wall such that the circumferential radiation dose distribution at the vessel wall is more evenly distributed. The energy attenuators are preferably constructed of a material which is denser than blood or any surrounding tissue, and will preferably be constructed of a stainless steel or a nickel titanium alloy to provide the desired energy attenuation. Use of a nickel titanium alloy is further advantageous in that such a material is fluoroscopically visible and may in turn be used to fluoroscopically visualize the radioactive sources and the catheter when introduced into a body lumen.

In one embodiment, the energy attenuator comprises a seed housing which is constructed of a material displaying superelastic properties, such as a nickel titanium alloy. The housing further includes an eccentric lumen for holding the radionuclides. The eccentric lumen forms an arcuate thick wall portion and an arcuate thin wall portion. By arranging the seed so that the thick wall portion faces radially outward, this thick wall portion will serve as an energy attenuator to provide a more uniform circumferential radiation dose distribution at the vessel wall. In another alternative embodiment, the seeds may be constructed to be cylindrical in geometry and the attenuators may comprise arcuate eccentric caps positioned around at least a portion of the seeds and arranged so that the caps face radially outward. In yet another alternative embodiment, the seeds may be contained within a radiation resistant polymeric housing, and the attenuator may comprise a nickel titanium clip which captures the seed within a polymeric channel.

In an alternative embodiment, spacers are provided between the radioactive sources and the vessel wall to provide for a more uniform dose distribution at the vessel wall. The spacers preferably distance the radioactive sources about 0.25 mm to about 0.5 mm from the vessel wall.

The invention includes a further alternative scheme for providing a more uniform circumferential radiation dose distribution at the vessel wall and includes a central or secondary radiation source that is surrounded by a plurality of primary radioactive sources which are placed in apposition with the vessel wall upon expansion of a balloon. Such a central source may be included, for example, on the tip of a guidewire which is positioned within a central lumen of a balloon catheter, about which the primary radioactive elements are distributed.

In some cases, it may be desirable to maintain the radioactive sources at a treatment region for an extended period of time. For example, in some cases it may be desirable to maintain the radioactive sources at a treatment site for up to about 20 minutes or more. In such cases, it is undesirable to fully occlude the body lumen, thereby preventing adequate blood flow to the distal body lumen beyond the occlusion. To provide adequate blood flow, the invention provides a variety of perfusion schemes that may be employed either with the self supporting embodiments, the balloon attachment embodiments or the sleeve attachment embodiments. For example, with catheters employing a balloon to deploy the radioactive sources, perfusion orifices may be included in the catheter body, both proximal and distal to the balloon, so that blood may bypass the balloon through a central lumen in the catheter body.

For the sleeve attachment embodiments which include both a balloon catheter and a slidable sleeve containing the radioactive sources, orifices are included in the catheter body proximal and distal to the balloon for allowing blood to bypass the balloon through a central lumen of the catheter. The sleeve containing the radioactive sources may also include orifices proximal to a radially expansible region to allow blood to flow through the sleeve and then through the catheter body orifices. In another embodiment, the sleeve may comprise a perfusion catheter having a radially deployable balloon containment region and at least one perfusion lumen, with the radioactive sources being distributed about the radially deployable region. In this manner, the balloon catheter may be inserted into the containment region of the perfusion catheter and the balloon expanded to move the radioactive sources radially outward. Upon inflation of the balloon, the blood may flow past the inflated balloon through the perfusion lumen(s) similar to the embodiments described in co-pending U.S. application Ser. No. 08/401,541, filed Mar. 10, 1995 (Attorney Docket No. 15509-7-2), the disclosure of which is herein incorporated by reference.

As previously mentioned, the radioactive sources may be self supporting, may be directly attached to a balloon or may be included in a sleeve which is slidably disposed over the balloon. In a preferred self supporting embodiment, the invention provides a radiation emitting catheter which employs an elastomeric or non-compliant balloon to radially deploy a single radioactive element, e.g., a radioactive element fashioned into an expansible cage structure. The balloon is attached to an elongate catheter body, and the radiation emitting element is attached to a long resilient push rod.

In the balloon attachment embodiments, the radioactive elements may be attached to an elastomeric or a non-compliant balloon in a variety of ways. For example, the radioactive elements may be secured to an outside surface of the balloon, i.e. by disposing the elements within polymeric channels or housings which in turn are attached to the balloon in an evenly distributed manner. An elastomeric membrane may optionally be disposed about the radioactive elements to prevent detachment of the elements during a procedure. The radioactive elements may also be placed on outside surface of the balloon by attaching the radioactive elements to an elastomeric membrane surrounding the balloon. Alternatively, the radioactive elements may be embedded within the elastomeric balloon in a variety of arrangement, such as by longitudinally aligning the elements parallel to the axis of the balloon. The elastomeric balloon will preferably be constructed of materials such as polyurethane, natural rubbers and synthetic rubbers. The non-compliant balloon will preferably be constructed of materials such as polyethylene, polyethylene terephthalate or nylon.

The balloon attachment embodiments may be configured to have a head which is attachable to the catheter body, with the head including the radioactive elements and the catheter body including the balloon. The attachable head configuration is advantageous in that it may be conveniently stored within a docking module which absorbs the radioactive energy emanating from the radioactive elements when the device is not in use. In this way, the head may be conveniently transported and stored until needed for a procedure. When needed, the catheter body may be fixedly attached to the head and the head advanced out of the docking module so that it may be introduced into the patient. The docking module containing the head will preferably be vacuum packaged or the package will contain a nitrogen environment to inhibit polymer degradation due to the radiation.

The catheter body will preferably include both an inflation lumen and a guidewire lumen. The guidewire lumen may terminate proximally to the balloon on the catheter body in a guidewire exit port or may continue through the catheter body to terminate at a proximal fitting. In this way, the catheter may be used in either a "rapid exchange" or an "over-the-wire" manner as is known in the art.

In one exemplary sleeve attachment embodiment, the structure comprises a radially expansible sleeve having an internal lumen for receiving the balloon. In this way, the balloon can be received within the sleeve and expanded to both radially expand the sleeve and to uniformly position the radioactive sources in apposition with the vessel walls. The sleeve can be configured in a variety of ways to be radially expansible including, providing a plurality of axial splits along the sleeve, forming the sleeve at least partially of an elastomeric material or a mesh, providing the sleeve with folds, and the like. Other suitable structures include cages, flexible elements aligned over the balloon, coils, and the like.

The expansible region is constructed so that the radioactive sources will be uniformly distributed within the vessel. Such uniform distribution may be accomplished, for example, by providing the sleeve with an offset slitting pattern. Alternatively, the radioactive elements may be contained within polymeric channels or housings which are separated by axial slits. An elastomeric membrane or webbing may be placed around the polymeric channels to maintain uniform spacing between the channels when the balloon is inflated. The sleeve may also comprise a flexible membrane which is folded until the balloon is inflated. In another alternative, the radioactive elements may be attached to an elastomeric membrane which surrounds the sleeve to place the radioactive elements about the sleeve.

The radioactive source employed with the slidable sleeve may also comprise a single seed which is folded into an expansible cage structure. The cage structure may be included within an expansible sleeve which is slid over a balloon, or the cage structure may be placed directly over a balloon. The cage structure may also be provided with an internal or an external elastomeric membrane to help evenly space the folded lengths of the seed when the cage structure is expanded and to assist in contracting the cage structure upon deflation of the balloon. The cage structure may be placed over only a portion of the balloon, or may extend beyond the ends of the balloon to provide a more uniform dose distribution at the vessel wall.

In another sleeve attachment embodiment, the invention provides an exemplary radiation-emitting sleeve catheter (RESC) having a shaft with a proximal end and a distal end. A radially expansible sleeve is disposed at the distal end of the shaft and includes an internal lumen for receiving a balloon on a balloon catheter. At least one radioactive source is provided and is secured to the radially expansible sleeve. In this manner, the RESC can be used in combination with a balloon catheter to radioactively treat a vessel. Following angioplasty with the balloon catheter, the sleeve is aligned over the balloon at the treatment site. The balloon is then inflated to radially expand the sleeve and to place the radioactive source adjacent the treated vessel walls.

The invention further provides various methods for performing angioplasty. Such procedures begin by inflating a conventional angioplasty balloon within a stenosed region of a blood vessel. The angioplasty balloon catheter is then removed in preparation for radiation treatment. For the self supporting embodiments, the single radioactive source (which is configured as an expandable cage structure that is connected to a rod) is placed over a balloon on a balloon catheter. The combined balloon catheter and cage structure are then introduced under fluoroscopic guidance to the previously dilated region and the balloon is inflated to expand the cage structure in apposition to the vessel wall.

When employing catheters having radioactive sources that are directly attached to a balloon, the catheter is introduced under fluoroscopic guidance to the previously dilated region and the balloon inflated to place the radioactive sources in apposition to the vessel wall. If the radioactive sources are included on a separate head, the head will be attached to the catheter body incorporating a balloon at its distal end, and the assembled catheter will be advanced to the desired region.

For the sleeve attachment embodiments, the radioactive sources are aligned over the deflated angioplasty balloon (or another balloon catheter) after vessel dilatation. The balloon is then reinflated to engage the radioactive sources directly against or in close proximity to the luminal wall of the treated region of the vessel. In one preferred aspect, the deflated balloon is withdrawn from the blood vessel following angioplasty, and the radially expansible sleeve with the radioactive sources while still in its shielded docking module is loaded over the shaft of the deflated balloon. After placement of the sleeve over a proximal portion of a balloon shaft, the deflated balloon is then reintroduced to the treated region of the blood vessel. The sleeve with its radioactive source is made to exit the shielded docking module and advanced and aligned over the balloon in the treatment region, after which the balloon is reinflated to bring the radioactive source into apposition with the vessel wall. Alternatively, a new balloon catheter may be pre-loaded with the sleeve prior to the angioplasty procedure and the combined device may be distally advanced to align with the treated region.

The radioactive sources in the self supporting configuration, the balloon attachment embodiments and the sleeve attachment embodiments will preferably emit beta radiation and will be maintained at the treatment region for a time in the range from about 1 minute to about 3 minutes to achieve a dose from about 5 Gy to about 50 Gy at the luminal surface of the body lumen. If necessary, the balloon catheter (and sleeve if employed) may include perfusion orifices as previously described to allow blood to flow through the vessel during treatment. With such perfusion orifices, longer dwell times are possible.

In cases where a central or secondary radiation source is employed in combination with the primary radioactive sources which are placed in apposition with the vessel wall, the method proceeds by introducing the angioplasty balloon over a first guidewire. Following angioplasty, the angioplasty balloon is removed and a balloon catheter or a combined balloon catheter (which may comprise the angioplasty balloon catheter) and sleeve are introduced over the first guidewire. The balloon is then inflated to place the primary radioactive sources that are self supporting or attached to the balloon or the sleeve in apposition with the vessel wall. The first guidewire is then removed and a second guidewire having the central radioactive source is introduced through the central lumen of the balloon catheter.

It will be appreciated that several of the elements of the various systems as just described may be interchanged depending upon the required treatment. Hence, the embodiments described herein provide a workable system which may be used to treat various body lumens with a radiation dose. A further understanding of the invention will be attained with reference to the following drawings.

BRIEF DESCRIPTION OF THE DRAWINGS

FIG. 1 is a side view of an exemplary RESC according to the present invention.

FIGS. 1A–1C are cross-sectional views of the RESC of FIG. 1 taken along lines A—A through C—C, respectively.

FIG. 2 is a perspective view of a distal end of the RESC of FIG. 1 placed over a balloon catheter according to the invention.

FIG. 3 is a perspective view of the distal end of the RESC of FIG. 1 when aligned over the balloon catheter of FIG. 2 according to the invention.

FIG. 4 illustrates the distal end of the RESC of FIG. 1 when radially expanded by the balloon catheter of FIG. 2 according to the present invention.

FIG. 4A is a cross-sectional view of the radially expanded distal end of the RESC of FIG. 4.

FIG. 22 is a side view of a distal end of an exemplary catheter having an elastomeric balloon and a plurality of radiation emitting elements attached thereto according to the present invention.

FIG. 22A is a cross-sectional view of the catheter of FIG. 22 taken along lines A—A when inflated within a vessel.

FIG. 23 illustrates the catheter of FIG. 22A when the elastomeric balloon is deflated.

FIG. 24 is a cross-sectional side view of a catheter system having a balloon catheter and a RESC disposed over the balloon catheter, with both the balloon catheter and the RESC having perfusion orifices according to the present invention.

FIG. 25 is a cross-sectional end view of the catheter system of FIG. 24 with the balloon inside the elastomeric sleeve deflated.

FIGS. 26–28 illustrate an exemplary method for providing radiation therapy while employing an angioplasty balloon catheter and the catheter system of FIG. 24 according to the present invention.

FIG. 44 is a perspective view of an elastomeric balloon catheter having a plurality of seeds embedded within the elastomeric balloon according to the present invention.

FIG. 45 is a cross-sectional side view of the catheter of FIG. 44.

FIGS. 46 and 47 illustrate cross-sectional end views of the elastomeric balloon and seeds of the catheter of FIG. 44 showing the balloon deflated and inflated, respectively.

FIG. 53 illustrates a self supporting single seed folded into an expansible cage structure according to the present invention.

FIG. 54A is a schematic side view of a balloon catheter having an expansible cage structure over a deflated balloon according to the invention.

FIG. 54B illustrates the balloon of FIG. 54A when inflated.

FIG. 55 is a graph illustrating the dose distribution provided by the cage structure of FIG. 54B.

FIG. 56A is a schematic side view of a balloon catheter having an expansible cage structure extending beyond ends of a deflated balloon according to the invention.

FIG. 56B illustrates the balloon of FIG. 56A when inflated.

FIG. 57 is a graph illustrating the dose distribution provided by the cage structure of FIG. 56B.

DESCRIPTION OF THE SPECIFIC EMBODIMENTS

Figure 5:
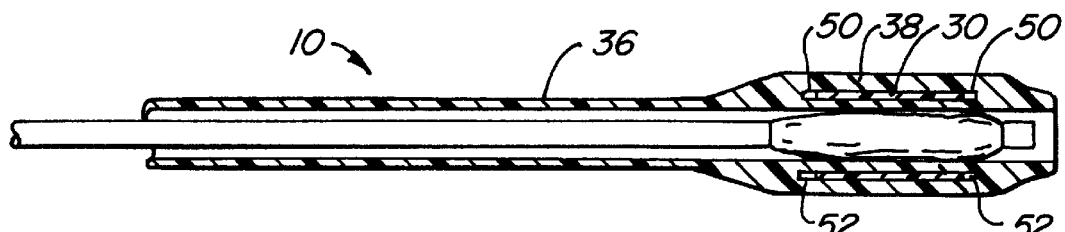
FIG. 5 illustrates a cutaway side view of one embodiment of a radially expansible sleeve having a radioactive source according to the present invention.

The invention provides apparatus and methods for performing angioplasty, and particularly for the internal irradiation of the treated vessel, post-dilatation. Apparatus of the invention include catheters or catheter systems which employ a balloon to place radioactive sources in apposition with a vessel wall. The invention covers embodiments where the radioactive sources are directly attached to the balloon, embodiments where the radioactive sources are attached to a sleeve which in turn is slidably disposed about the balloon, and radioactive sources that are self supporting and slidably adjusted about the balloon.

The sleeve attachment embodiments comprise both a balloon catheter and at least one radioactive source which is attached to or secured within a radiation-emitting sleeve catheter (RESC). Another alternative embodiment comprises a self supporting, single seed expandable cage attached to a push rod. By "self supporting" it is meant that the seed does not require the use of a supporting membrane, although such a membrane could optionally be included. With such configurations, either the RESC having the radioactive source(s) or the self supporting single seed cage may be aligned over the balloon so that inflation of the balloon will place the radioactive source(s) in apposition with a treatment region of the vessel previously dilated by a balloon.

Most commercially available balloon catheters may be used in combination with the invention. These include, for example, balloon catheters available from Advanced Cardiovascular Systems, Inc., Temecula, Calif. Such balloon catheters, which are well described in the medical literature, include an elongate catheter body and a balloon attached near a distal end of the catheter body.

The balloon attachment embodiments will preferably comprise a catheter having an elastomeric balloon to which the radioactive sources are secured, although in some cases a non-compliant balloon may be employed. Preferable materials for constructing such an elastomeric balloon include polyurethane, natural rubbers, synthetic rubbers, and the like. These materials should be able to withstand the effects of prolonged low-level radiation without substantial physical deterioration. The radioactive source may be directly attached to the elastomeric balloon or may be embedded in the balloon walls. Optionally, the radioactive sources may be constrained by an elastomeric sleeve or membrane to prevent them from detaching from the balloon.

Radioactive sources of the present invention include radioactive materials or radioisotopes emitting gamma ($\gamma$) or beta ($\beta$) radiation and sometimes a combination of both. Preferred radioisotopes include $^{192}$Iridium (half life of 74.2 days) emitting a spectrum of $\gamma$ plus $\beta$ radiation, $^{125}$Iodine (half life of 59.6 days) emitting $\gamma$ radiation, $^{90}$Strontium (half life of 28.1 years) and $^{90}$Yttrium (half life of 64.1 hours), both emitting $\beta$ radiation only. $^{90}$Strontium, which decays to $^{90}$Yttrium, may be a particularly attractive radioactive source in that both isotopes together, when reaching equilibrium, will emit $\beta$ radiation on a 1 to 1 activity basis, with the $^{90}$Strontium emitting low energy radiation (maximum of 0.54 Mev) and the $^{90}$Yttrium emitting high energy radiation (maximum of 2.27 Mev). As the short lived $^{90}$Yttrium decays to $^{90}$Zirconium, it is replenished by the decay of the long lived $^{90}$Strontium.

Such radioactive sources will be activated to levels suitable for the delivery of a predetermined dose of radiation to the treatment region of the vessel wall of about 5 Gray (Gy) to 50 Gy, more preferably from about 10 Gy to 20 Gy. Depending on the source, the time since its activation, and the geometrical arrangement of the source within the diseased vessel, the irradiation will be delivered in about 1 minute to 40 minutes, and more preferably from about 2 minutes to 3 minutes.

While gamma and beta radiation have shown similar results for the inhibition of neointimal hyperplasia in animal models, with comparable activation levels and total tissue dose, these two types of radiation are substantially different from each other. Gamma rays consist of high-energy photons with no electric charge and having high penetration powers, of the order of several centimeters in lead. Beta radiation, on the other hand consists of either electrons or positrons having a negative or positive charge, respectively, and can penetrate, for example, a few millimeters of aluminum or a few centimeters of acrylic polymer.

The radioactive sources may have a variety of shapes and configurations, and will usually comprise a plurality of discrete elements or a single element which is folded into an expansible cage structure. One exemplary embodiment of a radioactive source comprises a seed which is constructed of a housing and radionuclides within an axial lumen of the housing. The housing is preferably flexible in the transverse direction so that it may adequately traverse the tortuous path through a patient's vasculature. Containing the radionuclides within a housing is further advantageous in that the seeds may be reused. Seeds constructed in a sealed arrangement may be attached to or embedded within either an elastomeric balloon or a sleeve catheter. Other discrete elements which may be used with the invention comprise, for example, elongate ribs, ribbons, wires, and the like.

When the radioactive sources are secured to a balloon or a sleeve that in turn is placed over a balloon, or when a single self supporting radioactive source is arranged over a balloon, these radioactive source(s) should be aligned on or over the balloon so that upon inflation of the balloon, the radioactive sources will be placed in apposition with the treated vessel wall. Further, the self supporting radioactive source, or the radioactive sources that are secured to the balloon or to the sleeve, will preferably be aligned on or over the balloon so that when the balloon is inflated, the radioactive sources are substantially uniformly distributed over the treatment region of the vessel wall to uniformly irradiate the vessel wall.

Since the radioactive sources are positioned in such close proximity to the vessel wall, it will be possible to energize the radioactive elements to lesser initial activity levels than if they were located in the center of the vessel. Furthermore, when using a non-implantable radioactive source with a diameter substantially smaller than the vessel lumen, as proposed in the prior art, there is no assurance that the radioactive source will remain centrally located in the vessel lumen, thus potentially resulting in a non-uniform circumferential dose distribution in the diseased vessel. This non-uniformity is particularly detrimental when using β radiation which is markedly attenuated by substances such as blood, contrast agent, or other materials surrounding the radiation source, therefore exposing different sectors of the arterial tissue surrounding the lumen to substantially different irradiation doses. This non-uniformity is even more pronounced for vessels having larger lumens.

The invention covers other embodiments which help to provide a more uniform circumferential radiation dose distribution at a vessel wall. One exemplary way to provide such an improved dose distribution to the vessel wall is by slightly moving the source away from the wall, i.e. toward the center of the vessel, preferably by placing an energy attenuator between the radioactive source and the vessel wall. The attenuator preferably is constructed of a material which is denser than the surrounding blood and tissue. By attenuating the energy from the radioactive source in this manner, the vessel wall experiences an even more uniform circumferential radiation dose distribution.

An alternative way to improve the circumferential radiation dose distribution is by including a secondary radiation source which is surrounded by the primary self supporting single seed cage or the radioactive sources within the RESC or attached to the balloon. For example, a guidewire having a radioactive source may be positioned within a guidewire lumen of the balloon catheter so that the radioactive source will generally be centered relative to the radioactive sources of the self supporting cage, the RESC or balloon catheter when the balloon is expanded within the body lumen.

Typically, the self supporting single seed cage, or the distal end of the RESC or the balloon catheter, with the built in activated and sealed radiation source, will be appropriately shielded for the safety of the catheterization laboratory personnel and the patient. In the case of γ radiation, the shielding would comprise a substantial lead or depleted uranium enclosure, and in the case of β radiation, of a similar polymer enclosure, usually an acrylic polymer or the like, surrounded by an additional lead or the like shield, to stop the electromagnetic radiation (also called "Bremsstrahlung") generated as the β particles collide with the atoms in the polymer, as is common practice when handling such radiation sources.

In one aspect of the invention, the radioactive sources may be included on a catheter head which is attachable to a catheter body. In this manner, the head may be maintained within a docking module which absorbs the radiation energy until needed for a procedure. To perform the procedure, the catheter body is attached to the head and the head is then advanced into the patient's body from the docking module.

Another consideration in the selection of the radiation-emitting source material will be the half-life of its decay process. Radioisotopes with half-lives of the order of months and years will have a much longer useful shelf-life than other radioisotopes having half-lives on the order of only a few days or hours, in which case the time between their activation in a reactor and their use in the catheterization laboratory becomes of critical importance. On the other hand, such short half-life materials lend themselves to much easier disposal than those having the longer decay periods. The invention will preferably employ radioisotopes with relatively long half-lives so that the radioisotopes may be reused after a procedure.

The RESC will preferably have a distal portion which is radially expansible so that upon inflation of the balloon, the radioactive sources will be radially expanded toward the vessel walls. The distal portion can be fashioned to be radially expansible by including in its construction materials such as an elastomer, a mesh, a folded material, and the like, or constructing the distal portion out of a non-distensible material having an appropriate slitting pattern.

Referring now to FIG. 1 an exemplary embodiment of a radiation-emitting sleeve catheter (RESC) 10 will be described. The RESC 10 is constructed of a catheter body 12 having a proximal portion 14, a central portion 16, and a distal portion 18. The catheter body 12 will have a length depending on its desired use. Typically, the length will be from about 40 cm to 150 cm. The length of the distal portion will be at least long enough to cover the balloon. The outer diameter of the catheter body will usually be between about 1.4 mm and 2.3 mm, more usually being between about 1.6 mm and 2.0 mm. The catheter body 12 may be constructed of materials as described in co-pending U.S. application Ser. No. 08/222,143, filed May 1, 1994 (Attorney Docket No. 15509-2-2), the complete disclosure of which is herein incorporated by reference.

The proximal portion 14 is preferably constructed of a steel push rod 15 within a polymer sheath 19 as shown in cross-sectional view in FIG. 1C. Push rod 15 provides sufficient longitudinal stiffness for pushing RESC 10 into the vascular anatomy. A hub 17 is attached to a proximal end of the push rod. The central portion 16 is shown in cross-sectional view in FIG. 1B and is preferably constructed of a single lumen polymer tube (with or without stiffening elements such as braided steel wires or wire coils) that is attached to or integrally formed with the proximal portion 14. Extending through the central portion 16 is a central lumen 20 which includes a port 24 through which a balloon catheter may be introduced into the central lumen 20.

The distal portion 18 is shown in cross-sectional view in FIG. 1A and includes a plurality of axial slits 28 that allow the distal portion 18 to be radially expanded upon inflation of the balloon on the balloon catheter. The axial slits 28 are preferably axially aligned with the balloon on the balloon catheter. For most procedures, the axial slits 28 will allow the distal portion 18 to be radially expanded so as to engage the walls of the vessel, with the outside diameter of the distal portion usually being in the range from about 2 mm to 5 mm when radially expanded.

The distal portion 18 includes a plurality of outside lumens 21 into which a plurality of elongate radioactive elements 30 may be introduced. The elements may be constructed, for example, of materials such as those described in Youri Popowski et al., High Dose Rate Brachytherapy for Prevention of Restenosis After Percutaneous Transluminal Coronary Angioplasty: Preliminary Dosimetric Tests of a New Source Presentation, Int. J. Radiology Oncology Bio. Phys., Vol. 33, No. 1, pp 211–215, 1995; or Ron Waksman et al., Intracoronary Radiation Before Stent Implantation Inhibits Neointimal Formation in Stented Porcine Coronary Arteries, Circulation, Vol 92, No 6, Sep. 15, 1995, pp 1383–1386, the disclosures of which have previously been incorporated by reference. In some cases, the elements 30 may have sufficient transverse flexibility and longitudinal stiffness to provide rigidity to the distal portion of catheter during tracking through the vascular anatomy. Optionally, stiffening elements, such as metal bars, may be placed within some of the lumens 21 as described in, for example, U.S. patent application Ser. No. 08/222,143 (Attorney Docket No. 15509-2-2), previously incorporated by reference.

Although shown with four radioactive elements 30, the RESC 10 can be provided with more than four elements, with each of the elements 30 preferably being equally spaced apart. In this manner, when the distal portion 18 is radially expanded, the radioactive elements 30 are equally spaced over the treatment region of the vessel to provide a substantially uniform radiation treatment of the vessel wall. This can be most advantageously attained by using an offset slit pattern as taught in co-pending U.S. patent application Ser. Nos. 08/241,428, filed May 11, 1994, and 08/325,958, filed Oct. 20, 1994 (Attorney Docket Nos. 15509-2-3 and 15509-13, respectively), hereby incorporated in their entirety by reference. While radioactive elements 30 in lumens 21 are shown aligned substantially with the axis of the RESC 10, it is envisaged that radioactive elements 30 and lumens 21 may have a helical construction (not shown) allowing for a different distribution of the radioactive elements 30 in the lumen of the vessel when the elements 30 are deployed.

Another particular advantage of RESC 10 is that the radioactive elements 30 may be placed in close proximity to the vessel wall. In this way, radioactive elements with lower radioactive activation levels can be provided. In another advantage, the radioactive elements are uniformly distributed against the treated region, both longitudinally and circumferentially. This, in turn, allows for a more uniform radiation treatment of the vessel. A further advantage of RESC 10 is that one size of RESC 10 can be employed to treat vessels of various sizes. To irradiate a treatment region, the same balloon catheter used to perform angioplasty in the diseased region is employed to radially expand RESC 10. In this way, proper expansion is generally assured since the same balloon employed for the primary procedure is also used to deploy the radioactive elements 30.

Cooperation of RESC 10 with a balloon catheter 34 having a shaft 33 and a balloon 32 will be described with reference to FIGS. 2–4. RESC 10 is sized so that it may be axially advanced over the shaft 33 as illustrated in FIG. 2. With the balloon 32 deflated, RESC 10 may be advanced to position the distal portion 18 over the balloon 32 as shown in FIG. 3. With RESC 10 in place, the balloon 32 is inflated to radially expand the distal portion 18 as shown in FIG. 4. As best shown in FIG. 4A, inflation of the balloon 32 will move the elements 30 radially outward so that they may engage the vessel wall.

To fluoroscopically align the angioplasty balloon with the radioactive expansible portion of RESC 10, it may be desirable to provide spaced apart markers (not shown) on RESC 10 as disclosed in U.S. Pat. No. 5,336,178, herein incorporated by reference, and co-pending U.S. patent application Ser. No. 08/222,143 (Attorney Docket No. 15509-2-2), previously incorporated by reference, and a central marker 37 (see FIG. 2) on balloon catheter 34. In this manner, central marker 37 may be positioned between the spaced apart markers on the RESC 10 to align the RESC 10 with the central marker 37 on balloon catheter 34. Alternatively, or in addition to the spaced-apart markers described above, it may be desirable to provide end marker pairs 50, 52 on RESC 10 (FIGS. 5 and 6) to indicate the ends of the radioactive elements 30 of RESC 10. Such end markers on the RESC 10 may then be aligned with the central marker 37 on the balloon catheter by visually centering the central marker 37 between the RESC end marker pairs. A third alignment scheme would involve aligning the RESC end marker pairs with widely spaced apart markers 39 (shown in phantom line in FIGS. 2 and 6) on the balloon catheter shaft indicating the ends of the cylindrical portion of the balloon. These marker schemes and alignment methods may be particularly advantageous when using β radiation since the β radiation from the source will be absorbed by the surrounding tissue and will not interfere with or be visible in the fluoroscopic image. On the other hand, when using a source emitting γ radiation, there may no longer be a need for additional markers on the RESC 10, since the source would absorb the X-radiation from the fluoroscope rendering the source itself radiopaque and thus fluoroscopically visible. The radioactive elements themselves would therefore provide a natural visualization means enabling centering with a central balloon marker 37 or spaced-apart balloon markers 39, using standard catheterization laboratory fluoroscopy methods.

Figure 6:
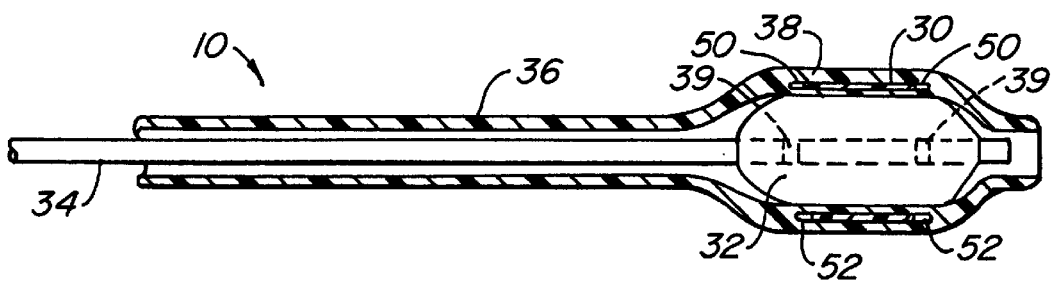
FIG. 6 illustrates the sleeve of FIG. 5 being radially expanded by a balloon.
Figure 7:
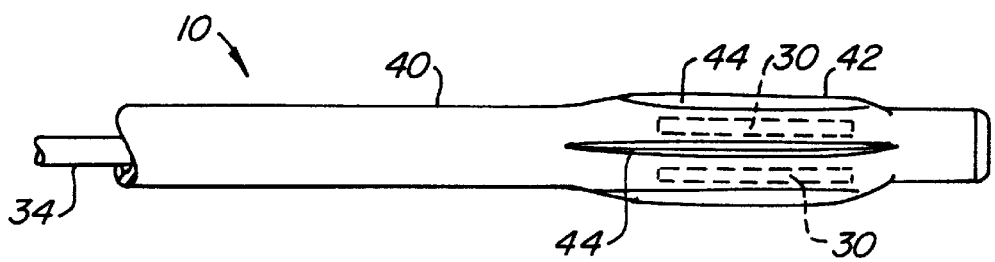
FIG. 7 illustrates a side view of an alternative embodiment of a radially expansible sleeve according to the present invention.
Figure 8:
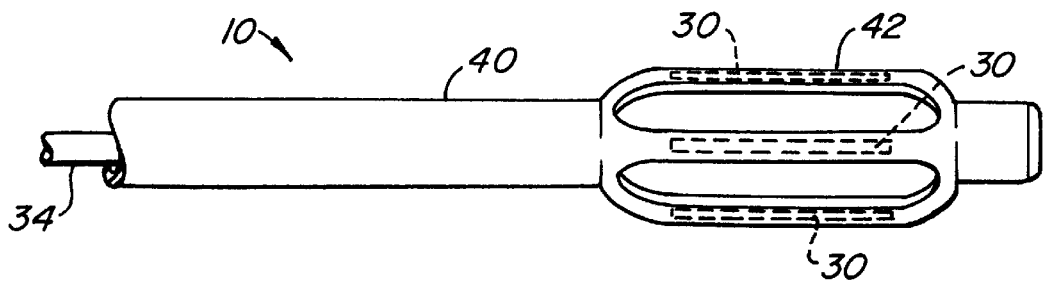
FIG. 8 illustrates the sleeve of FIG. 7 in a radially expanded state.

Alternative embodiments of RESCs are illustrated in FIGS. 5–12 and are constructed essentially identical to RESC 10 of FIG. 1 except for the construction of the distal portion 18. Referring first to FIGS. 5 and 6, an alternative embodiment of a distal portion 36 will be described. The distal portion 36 includes a radially expansible region 38 having the radioactive elements 30. As best shown in FIG. 6, when the balloon 32 is inflated while within the expansible region 38, the walls of the expansible region 38 radially expand and become thinner. Radial expansion of the region 38 radially translates the elements 30 until the expansible region 38 comes in contact with the vessel wall. The expansible region 38 is constructed of an elastomeric material, such as a medical grade synthetic rubber, Santoprene™ (Advanced Elastomeric Systems) or a thermoplastic elastomeric polyurethane sold under the trademark Tecoflex™ by Thermetics, Inc. or Kraton™ by Shell Chemical Co. Construction of the distal portion 36 is described in greater detail in co-pending U.S. patent application Ser. No. 08/325,958 (attorney docket no. 15509-13), previously incorporated herein by reference. optionally, as further described in U.S. patent application Ser. No. 08/325,958 the expansible region 38 can be constructed to include a porous matrix material containing a drug interspersed therein. In this way, delivery of a variety of therapeutic agents can be provided while simultaneously providing radiation therapy. Referring to FIGS. 7 and 8, a further alternative embodiment of a distal portion 40 of RESC 10 will be described. The distal portion 40 includes a radially expansible region 42 having a plurality of folds 44. The radially expansible region 42 can be constructed of any non-compliant polymeric material having folds or pouches formed integrally with the polymeric material as taught in co-pending U.S. patent application Ser. No. 08/401,541, filed Mar. 10, 1995, previously incorporated by reference. The radially expansible region 42 is radially expanded by the balloon catheter 34 as shown in FIG. 8. As the balloon catheter 34 is inflated, the folds 44 expand to increase the surface area of the expansible region 42 and allow the radioactive elements 30 (shown in phantom line) to move radially outward toward the vessel wall.

Figure 9:
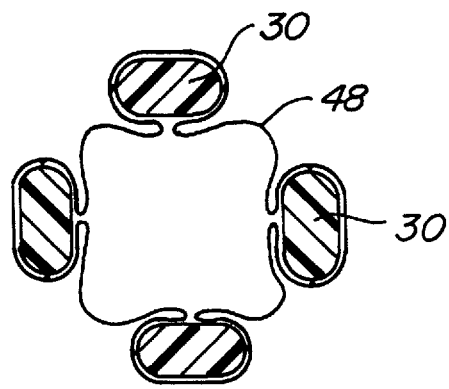
FIG. 9 illustrates a cross-sectional view of a further alternative embodiment of a radially expansible sleeve having a radioactive source according to the present invention.
Figure 10:
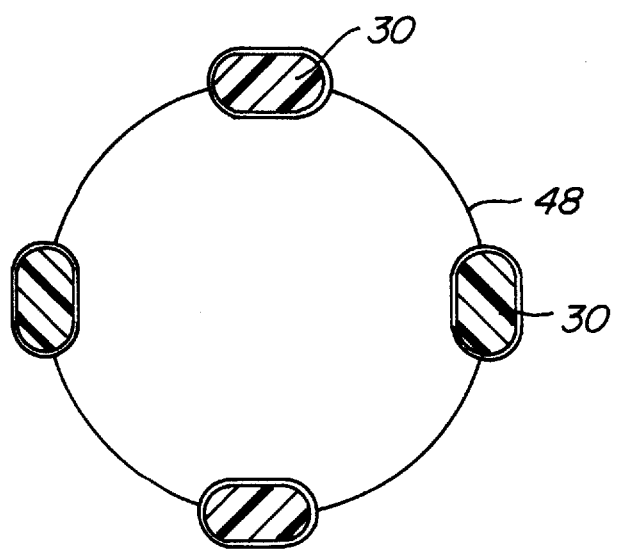
FIG. 10 illustrates the sleeve of FIG. 9 when radially expanded.

Referring to FIGS. 9 and 10, still a further alternative embodiment of a distal portion 46 of the RESC 10 will be described. The elements 30 are held within a sleeve 48 which is folded to hold the elements 30 close together as illustrated in FIG. 9, When the balloon is expanded, the sleeve 48 unfolds as illustrated in FIG. 10.

Figure 11:
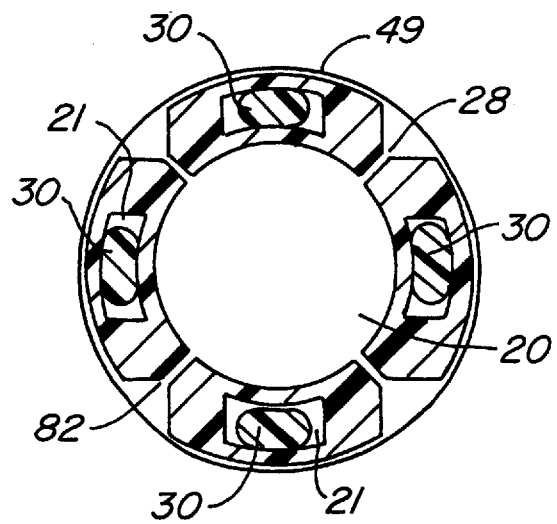
FIG. 11 illustrates the radiation emitting sleeve catheter of FIG. 1A surrounded by an elastomeric tubular sheath.
Figure 12:
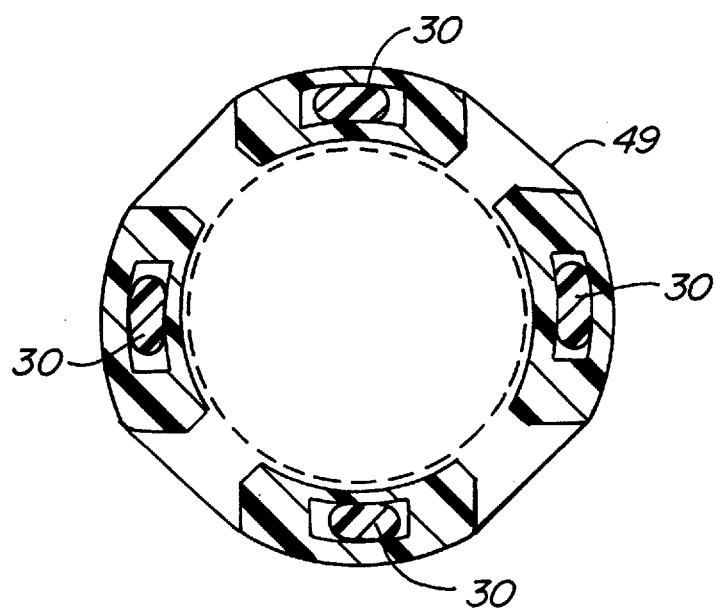
FIG. 12 illustrates the radiation emitting sleeve catheter of FIG. 11 when radially expanded.

Another alternative configuration of a distal portion 46 of RESC 10 is shown in FIGS. 11 and 12 wherein the portion of the catheter having slits 28 is enclosed by an elastomeric tubular sheath 49. Sheath 49 may be constructed of an elastomeric material, such as a medical grade synthetic rubber, Santoprene™ (Advanced Elastomeric Systems) or a thermoplastic elastomeric polyurethane sold under the trademark Tecoflex™ by Thermetics, Inc. or Kraton™ by Shell Chemical Co. One advantage of sheath 49 is that it will preclude a "winged" deflated balloon from getting caught in slits 28 when moving the balloon catheter relative to RESC 10. Also, the elastomeric tubular sheath 49 would urge radioactive elements 30 and distal portion 18 of catheter body 12 to contract uniformly following deflation of the balloon.

Other embodiments of radially expansible regions that would be capable of including a radioactive source according to the invention are described in co-pending U.S. patent application Ser. No. 08/222,143 (Attorney Docket No. 15509-2-2), filed May 1, 1994, previously incorporated by reference. For example, described in U.S. patent application Ser. No. 08/222,143 is a distal portion having a plurality of elongate slits formed in a webbed pattern and which can optionally be provided with an infusion array for delivering an agent to the treatment region. The webbed pattern allows the radioactive material to be uniformly distributed against the treatment region of the vessel wall.

Figure 13:
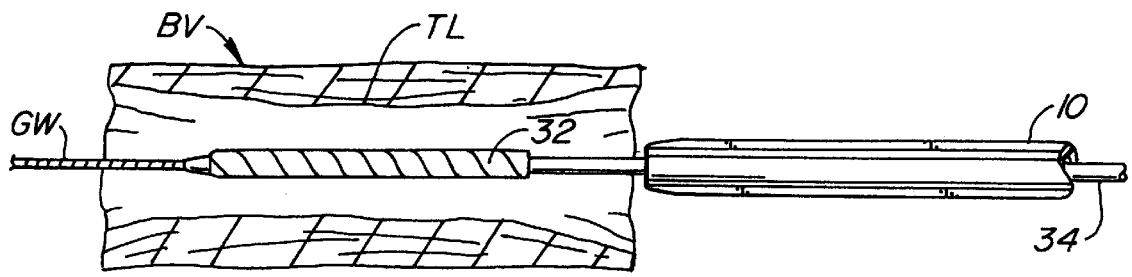
FIGS. 13–15 illustrate an exemplary method irradiating an angioplasty treatment site by aligning a radioactive, radially expansible sleeve over a balloon and inflating the balloon.
Figure 14:
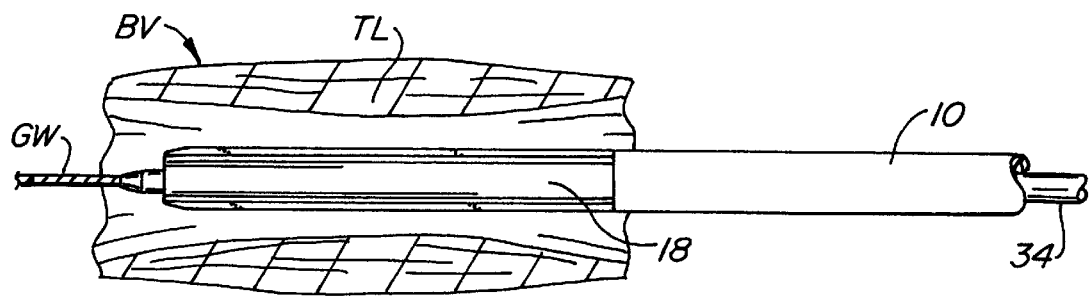
Figure 15:
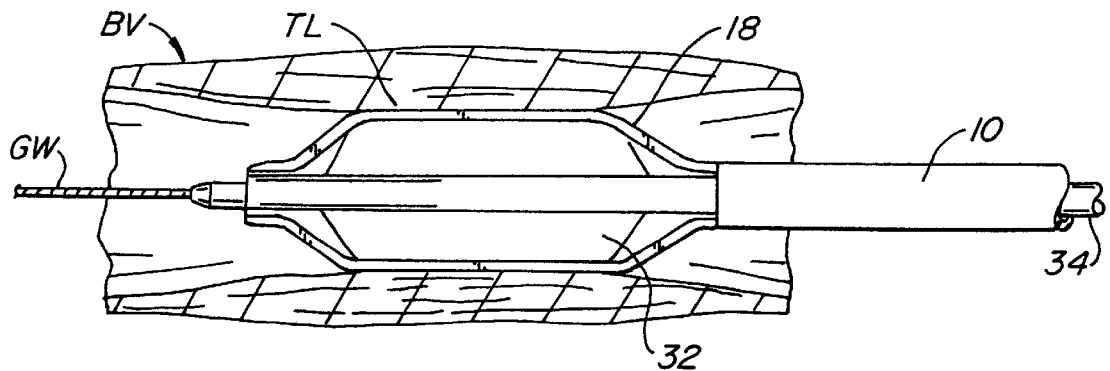

Referring to FIGS. 13–15, an exemplary method for performing angioplasty using RESC 10 and the balloon catheter 34 will be described. Initially, an incision is made in the femoral artery using the Seldinger procedure. A guide catheter is then inserted through an introducer sheath over a first guide wire up to a coronary ostium in the conventional manner. A second guidewire GW is then introduced through the guide catheter until reaching a target location TL in a blood vessel BV in the conventional manner. Balloon catheter 34 is then advanced over the guidewire GW to the target location TL where balloon 32 is inflated to perform angioplasty in the conventional manner.

The RESC 10 will preferably be loaded on the balloon catheter 34 following the primary angioplasty procedure in order to minimize the dwell time of the RESC 10 in the vasculature, although in some cases the RESC 10 may be pre-loaded on the balloon catheter prior to the primary angioplasty procedure. Thus, following the primary angioplasty procedure, with the guidewire GW remaining in place, the angioplasty catheter is fully withdrawn from the patient. RESC 10, with its primary shielding (not shown) still in place, is then loaded on the balloon catheter by inserting the distal end of the balloon catheter in opening 24 of RESC 10. Following the removal of the primary shielding, both catheters are rapidly introduced into the patient's vasculature through the guide catheter, preferably with the balloon catheter 34 leading, so that the balloon catheter 34 reaches the target location TL in the blood vessel BV over the guide wire GW in a generally conventional manner as shown in FIG. 13.

The use of a movable secondary shielding arrangement over the radioactive portion of the RESC 10 or a shielded guide catheter may not be practical due to the substantial shield thickness needed to provide significant or even adequate shielding when using either β or γ radiation, and the human vasculature will generally not accommodate such increases in hardware size. Therefore, it is important that traversing the RESC 10 to the treatment region be done in a rapid manner and that the radiation emitting portion of the catheter be kept in motion at all times except during the therapy period, to minimize the patient's exposure to unwanted radiation.

One exemplary embodiment of a primary shielding arrangement comprises a docking module into which the radiation emitting portion of the catheter is kept during transportation and storage. Such a docking module is described hereinafter with reference to FIGS. 51 and 52.

After the balloon catheter 34 is positioned at the target location TL by fluoroscopic observation (with balloon 32 still deflated), RESC 10 is advanced distally as shown in FIG. 14 until the distal region 18 is fluoroscopically aligned over balloon 32. Fluoroscopic alignment will preferably proceed according to one of the alignment schemes previously described in connection with FIGS. 2, 5, and 6.

After positioning has been achieved, balloon 32 is again inflated, engaging distal region 18 of the RESC 10 against the wall of the blood vessel BV by urging elements 30 into engagement with the vessel wall as shown in FIG. 15. Depending on the type of radioactive material and its activation level, the balloon 32 will remain inflated for about 1 to 3 minutes, usually 2 to 3 minutes. In other cases, the balloon may remain inflated for up to about 30 minutes. RESC 10 can be provided with a perfusion lumen as described in co-pending U.S. patent application Ser. No. 08/401,541 (Attorney Docket No. 15509-7-2), previously incorporated by reference, to allow blood to flow through the vessel for treatments times exceeding about 3 minutes. Optionally, a drug or an agent can be delivered to the target location TL during the irradiation procedure as previously described.

Figure 51:
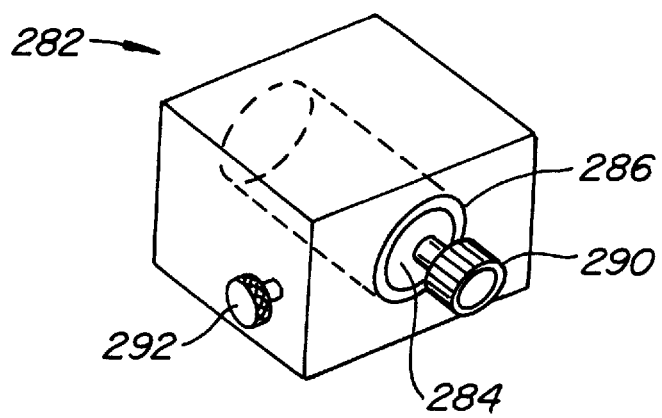
FIG. 51 is a perspective view of an exemplary docking module which may be employed to house radioactive elements of a catheter system according to the present invention.
Figure 52:
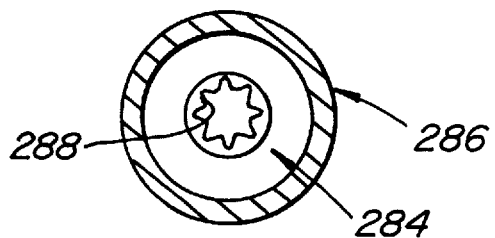
FIG. 52 is a cross-sectional end view of shielding employed by the docking module of FIG. 51.

After irradiation, the balloon 32 is deflated and the RESC 10 and the balloon catheter 34 are rapidly withdrawn from the patient and the primary shield, such as the docking module described in connection with FIGS. 51 and 52, is re-positioned over the radiation emitting portion of RESC 10 to contribute to the safety of the procedure, both for the patient and the catheterization laboratory personnel.

Figure 16:
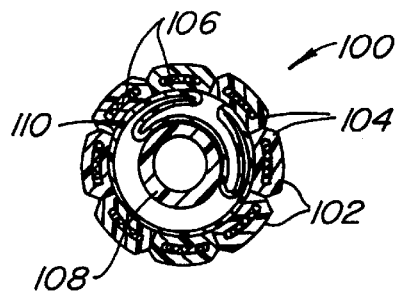
FIG. 16 is a cross-sectional end view of an alternative RESC which is positioned over an angioplasty balloon catheter according to the present invention.
Figure 16A:
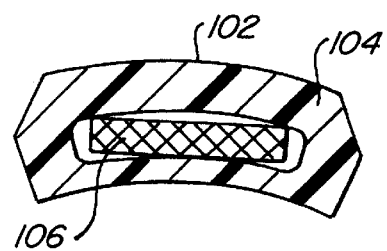
FIG. 16A is a more detailed view of one of the radiation emitting elements of the RESC of FIG. 16.
Figure 17:
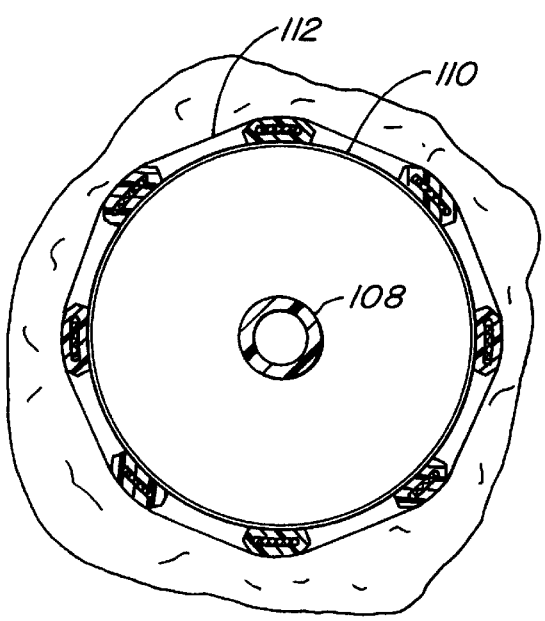
FIG. 17 illustrates the RESC of FIG. 16 when expanded within a vessel wall by the angioplasty balloon.

Referring to FIG. 16, an alternative embodiment of a RESC 100 will be described to illustrate the dose distribution within a vessel. RESC 100 is similar to RESC 10 of FIG. 1 except that RESC 10 includes eight radioactive elements 102. Each radioactive element 102 includes a polymeric housing 104 and a radionuclide 106. A detailed view of one of the radioactive elements 102 is illustrated in FIG. 16A. As shown in FIGS. 16 and 17, a standard PTCA balloon 108 is positioned within RESC 100. Balloon catheter 108 includes a balloon 110 which may be inflated to the configuration illustrated in FIG. 17 to radially deploy radioactive elements 102 against a vessel wall 112.

Figure 18:
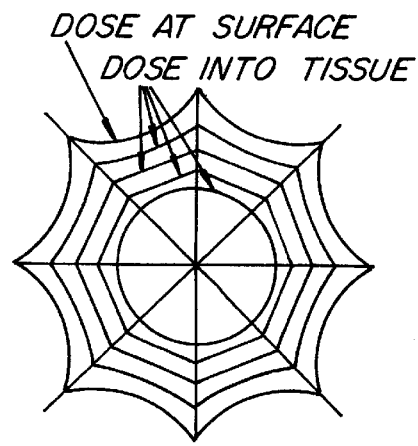
FIG. 18 is a polar graph illustrating the radiation dose delivered by the RESC of FIG. 17 at various tissue depths.

Referring to FIG. 18, the dose distribution provided by radioactive elements 102 when adjacent a vessel wall (as illustrated in FIG. 17) is shown at the luminal surface and at various depths into the vessel tissue. FIG. 18 illustrates in a polar coordinates graph that the dose at the surface of the luminal wall is non-uniform. However, the dose becomes progressively more uniform as the distance from the radioactive sources increases. Hence, one way to achieve a more uniform dose at the luminal wall surface is to, either slightly move the radioactive elements away from the vessel wall, i.e. toward the center of the vessel, or to place radiation attenuator elements between the radioactive elements and the vessel wall. When spacing the radioactive elements from the vessel wall, the spacing will preferably be in the range from about 0.25 mm to about 0.5 mm, and more preferably from about 0.3 mm to about 0.4 mm.

Figure 19:
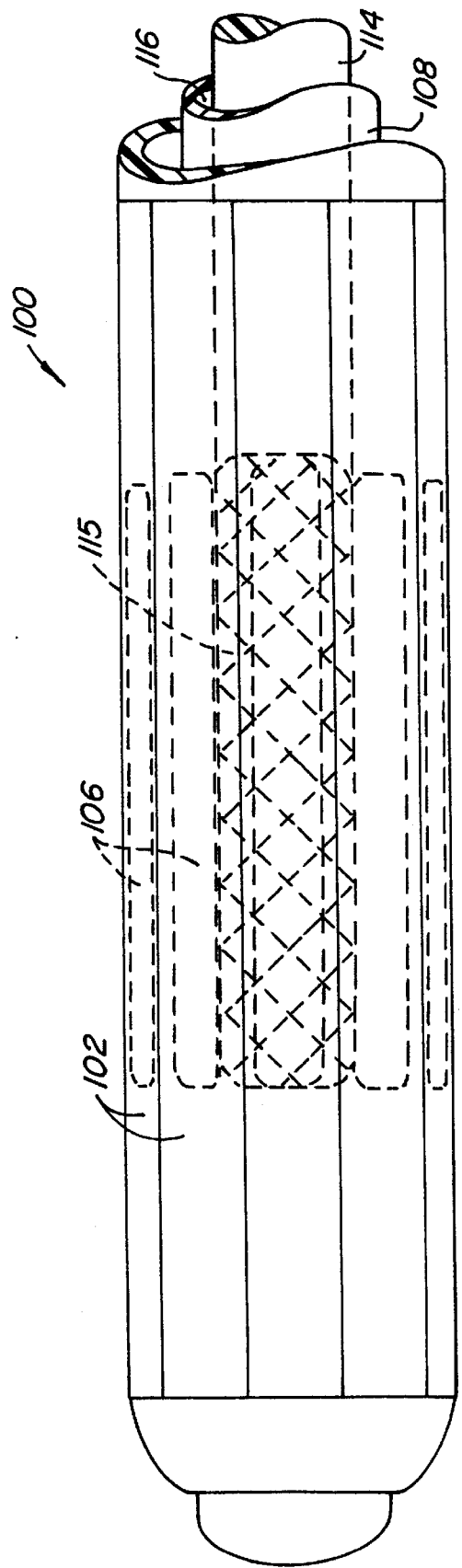
FIG. 19 is a side view of the RESC of FIG. 16 having a guidewire with a radiation emitting source.
Figure 20:
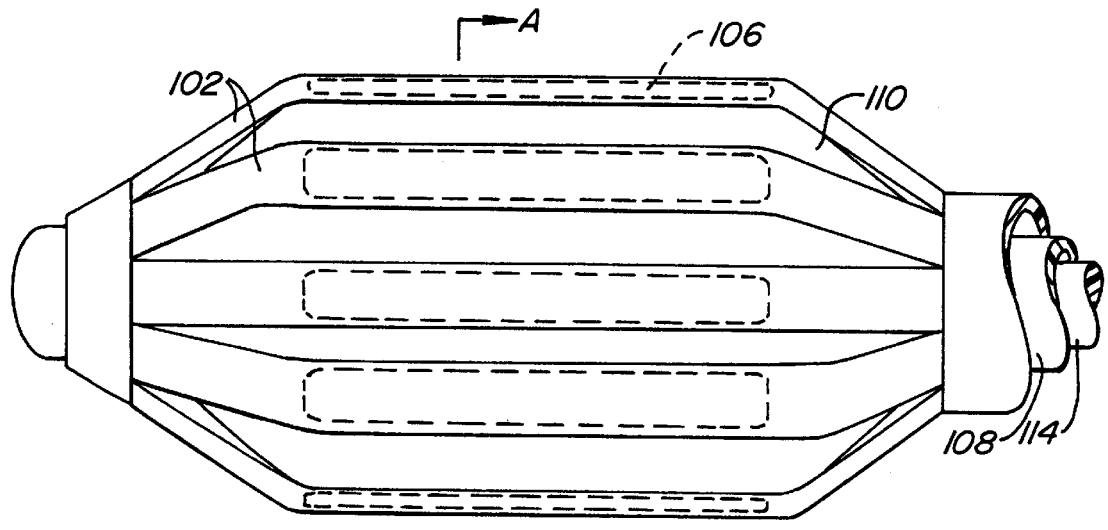
FIG. 20 illustrates the RESC of FIG. 19 when the angioplasty balloon is inflated.
Figure 20A:
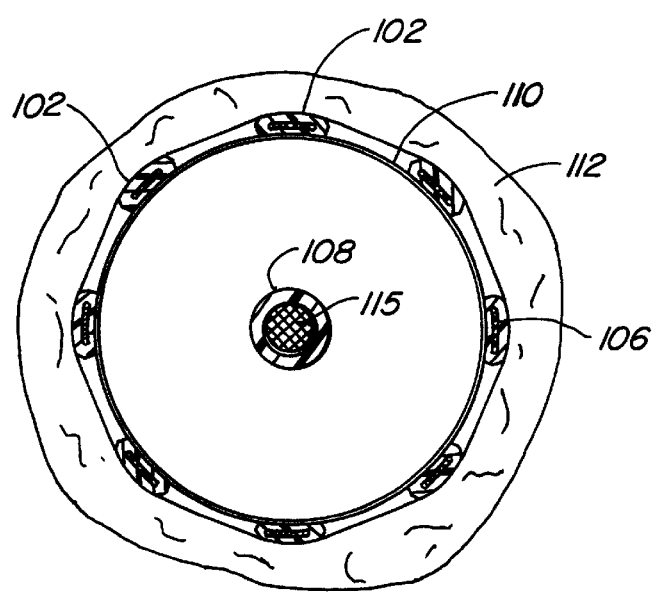
FIG. 20A is a cross-sectional view of the RESC of FIG. 20 taken along lines A—A when radially expanded within a body lumen.

Alternatively, to provide a more uniform circumferential radiation dose distribution at the luminal surface of the vessel wall, the invention employs in one embodiment, a guidewire 114 having a secondary radioactive source 115 as best illustrated in FIGS. 19 and 20A. Secondary radioactive source 115 on guidewire 114 is positioned within a lumen 116 of balloon catheter 108. As illustrated in FIGS. 20 and 20A, when balloon 110 is inflated, secondary radioactive source 115 is generally centered within vessel wall 112. In this manner, the radiation supplied by secondary radioactive source 115 assists to even out the circumferential radiation dose distribution at vessel wall 112.

When inflating balloon 110, it is desirable to maintain radioactive elements 102 uniformly distributed about the periphery of balloon 110. Such uniformity may be maintained, for example, by constraining radioactive elements 102 by an elastomeric sleeve or membrane (see FIGS. 11 and 12) so that they will be circumferentially uniformly separated when balloon 110 is inflated. Alternatively, elements 102 may be provided within a folded sleeve as previously described in connection with FIG. 9.

RESC 100 may be employed to radioactively treat a body lumen as follows. Initially, angioplasty is performed on a diseased area of the vessel as previously described in connection with FIG. 13, and the angioplasty balloon catheter is removed from the patient. RESC 100 is then positioned over the same (or another) angioplasty balloon catheter and introduced over the guidewire similarly to the procedure previously described in connection with FIG. 14. The guidewire is then removed and guidewire 114 having the secondary radioactive source 115 is introduced through balloon catheter 108 until the secondary source 115 is longitudinally aligned with radionuclides 106. Fluoroscopic visualization may be used in this process. Balloon 110 is then inflated for a time in the range from about 1 minute to about 3 minutes to achieve a dose of from about 5 Gy to about 50 Gy at the luminal surface of the body lumen.

Figure 21:
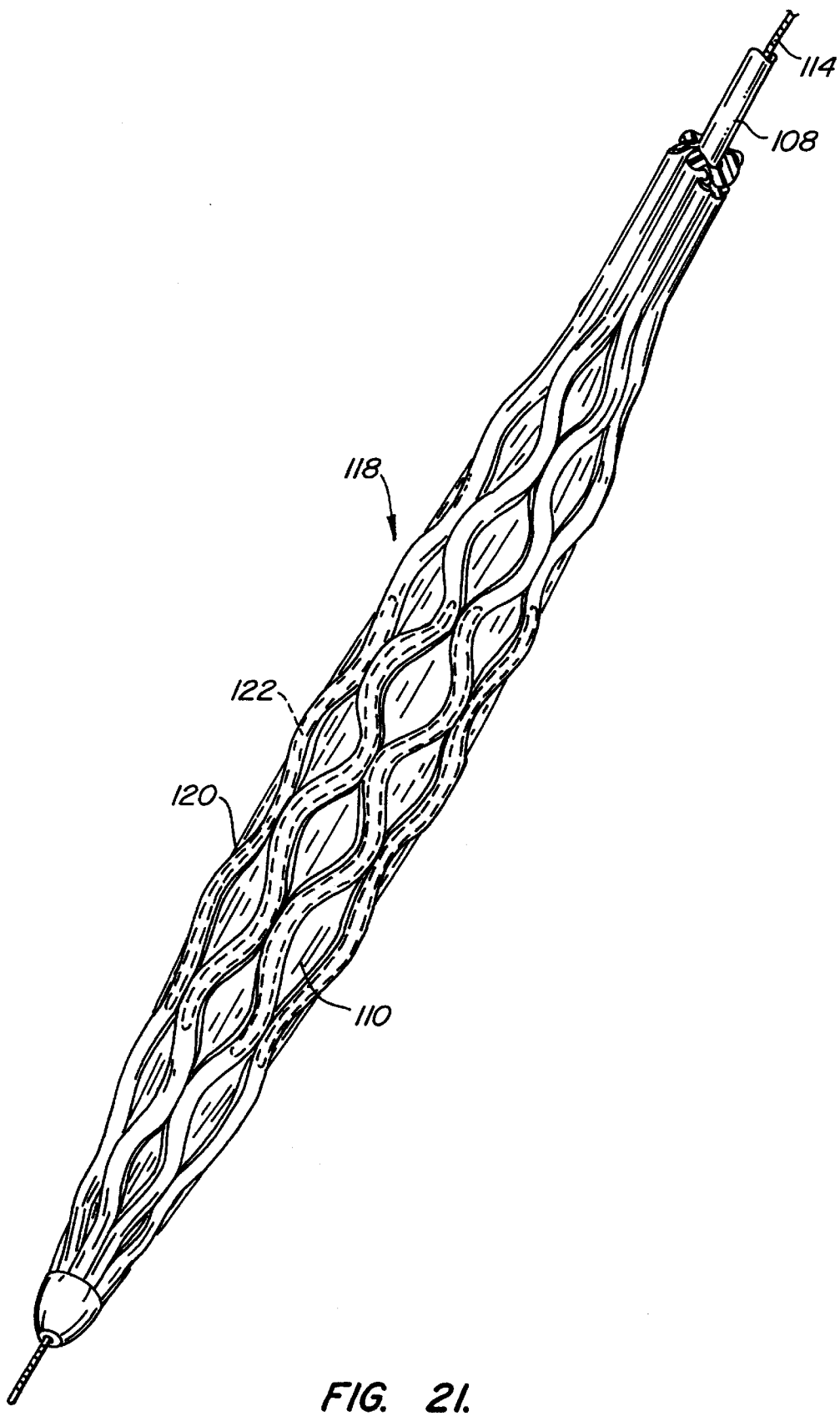
FIG. 21 is still a further alternative embodiment of a RESC having an expansible region fashioned to have an offset slitting pattern according to the present invention.

One alternative embodiment of an RESC 118 which may be employed to uniformly position radioactive elements 120 about a balloon is illustrated in FIG. 21. Radioactive elements 120 are fashioned to have an offset slitting pattern so that a plurality of radionuclides 122 are generally evenly distributed about balloon 110 of balloon catheter 108. The guidewire 114 with a radioactive tip may be employed to provide a secondary radiation source as previously described in connection with RESC 100.

Referring now to FIG. 22, an alternative embodiment of a radiation catheter 124 will be described. Radiation catheter 124 includes a catheter body 126 (only a distal portion of which is shown) and an elastomeric balloon 128. Attached to elastomeric balloon 128 are a plurality of radioactive elements 130. Radioactive elements 130 may comprise any of the radioactive elements as described herein. For convenience of discussion, radioactive elements 130 will be configured to be essentially identical to radioactive elements 102 and are constructed of polymeric housings 104 and radionuclides 106.

One particular advantage of radiation catheter 124 is the inclusion of elastomeric balloon 128. By constructing balloon 128 of an elastomeric material, apposition of radioactive elements 130 against the vessel wall can be achieved by inflating the balloon to a given size which is determined by the volume of fluid (such as saline solution) which is injected into the catheter. In this manner, radioactive elements 130 may be confidently deployed to a known location relative to catheter body 126. Furthermore, the elastomeric balloon 128 serves to center catheter body 126 within a vessel 132 as illustrated in FIG. 22A so that a guidewire 134 with a secondary radioactive source is centered within vessel 132 to provide a more uniform circumferential radiation dose distribution as previously described.

As shown in FIG. 23, when elastomeric balloon 128 is deflated, its wall thickness increases. Balloon 128 will preferably be constructed of an elastomeric material such as polyurethane, or other elastomeric materials including natural and synthetic rubbers. One acceptable polyurethane balloon catheter is manufactured by World Medical Manufacturing Corporation, Sunrise, Fla. and is described in U.S. Pat. No. 5,522,961, the disclosure of which is herein incorporated by reference. The radioactive elements 130 are attached to balloon 128 at discrete attachment points as shown in FIG. 22A so that when balloon 128 is inflated, the radioactive elements 130 will be evenly distributed around the circumference of the balloon, regardless of the configuration and thickness of any atheromatous material present in the vessel. Elastomeric balloon 128 will be preferably constructed of a material that is able to withstand a low level of radiation over an extended period of time without substantial degradation. Such materials may include, for example, ethylene propylene rubber (EPR), ethylene propylene dyene rubber (EPDM), and the like.

Before radioactively treating a body lumen with radiation catheter 124, the body lumen will preferably undergo a conventional angioplasty procedure as previously described. Radiation catheter 124 is then introduced over the guidewire until balloon 128 is at the treatment region. Fluoroscopic imaging will preferably be employed to help locate balloon 128 relative to the treatment region.

Optionally, the guidewire may then be replaced with guidewire 134 having a radioactive source which is longitudinally aligned with radioactive elements 130. Balloon 128 is inflated to place radioactive elements 130 in apposition to vessel 132 as previously described. Preferably, balloon 128 will remain inflated for a time in the range from about 1 minute to about 3 minutes to achieve a dose from about 5 Gy to about 50 Gy at the luminal surface of vessel 132.

In some cases, it may be desirable to maintain a radioactive source at a treatment region for longer than about 3 minutes. In such cases, it will be desirable to provide a form of perfusion during the delivery of the radiation to prevent ischemia in the distal tissue of the artery. One exemplary embodiment of the catheter system 136 for providing such perfusion is illustrated in FIG. 24. System 136 comprises a RESC 138 and a balloon catheter 140. RESC 138 may be constructed essentially identical to RESC 10 except that RESC 138 includes a plurality of perfusion orifices 142 proximal to the radioactive elements. Balloon catheter 140 is similar to a conventional angioplasty balloon catheter except that it includes a plurality of proximal perfusion ports 143 and distal perfusion ports 144. In this manner, when the balloon on catheter 140 is inflated within a vessel, blood flows through orifices 142 of RESC 138 and then through the proximal perfusion ports 143. The blood then passes through balloon catheter 140 and exits both through distal perfusion ports 144 and through the distal end of the central lumen of balloon catheter 140 as shown. Suitable balloon catheters include the ACS Flowtrack™ or the Lifestream™ catheters.

As illustrated in FIG. 25, RESC 138 will preferably also include an elastomeric membrane 146 to which radioactive elements 148 are discretely attached. In this manner, when the balloon is inflated, radioactive elements 148 will remain approximately equally spaced circumferentially within the vessel.

Referring to FIGS. 26–28, an exemplary method for treating a vessel with catheter system 136 will be described. Initially, a conventional angioplasty procedure is performed using a perfusion balloon catheter as mentioned above by introducing a perfusion balloon catheter 140 over a guidewire 152 (see FIG. 26) as is known in the art. Catheter 140 is then removed from the patient and the combined RESC 138 and balloon catheter 140 are tracked over guidewire 152 to the treatment region as illustrated in FIG. 27. Alternatively, the deflated perfusion balloon 140 is left in place at the treatment site and the RESC 138 is advanced over the perfusion balloon 140. Preferably, fluoroscopic imaging will be employed to align radioactive elements 148 with the balloon and the treated region. The balloon on catheter 140 is then inflated to place radioactive elements 148 in apposition to the vessel wall as illustrated in FIG. 28. Optionally, guidewire 152 may be pulled back so that blood will flow both through orifices 142 and through perfusion ports 143 and 144 as shown.

Figure 29:
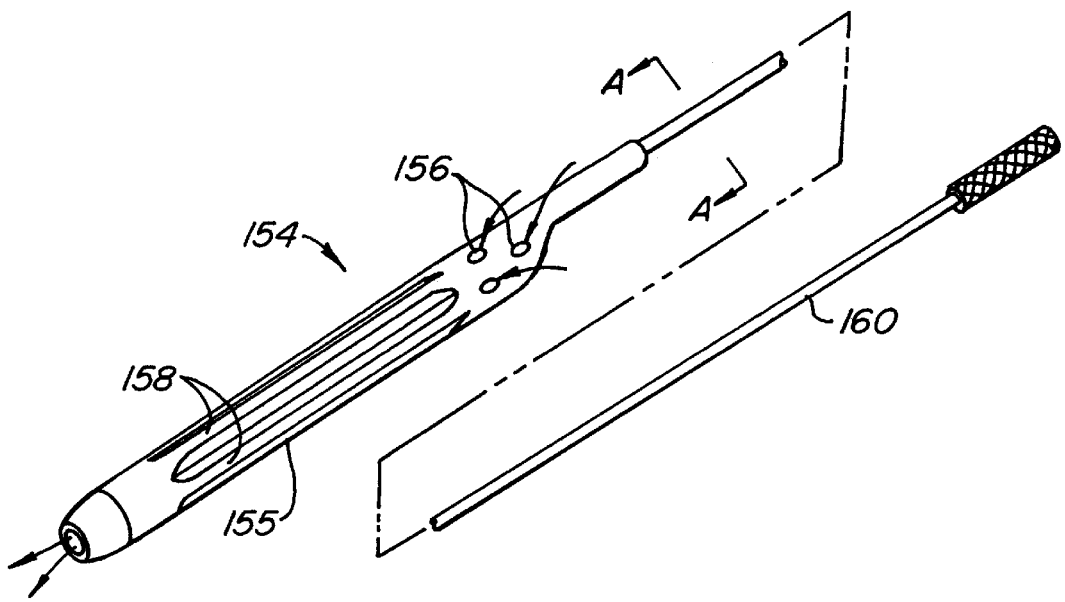
FIG. 29 is a perspective view of an alternative RESC having a short sleeve and a push rod.
Figure 29A:
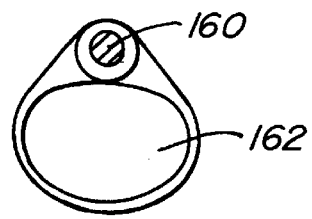
FIG. 29A is a cross-sectional side view of the RESC of FIG. 29 taken along lines A—A.

Referring to FIGS. 29 and 29A, another exemplary embodiment of a short sleeve RESC 154 with or within perfusion orifices 156 will be described. RESC 154 includes a radially deployable region 155 and is constructed similar to the sleeve catheter described in copending U.S. application Ser. No. 08/551,932, filed Oct. 23, 1995 (Attorney Docket Number 15509-002900), the disclosure of which is herein incorporated by reference. RESC 154 further includes a plurality of radiation emitting elements 158 at a deployable region 155. Radiation emitting elements 158 may be fashioned to be similar to those set forth in this application. RESC 154 further includes a push rod 160 and a central aperture 162 for receiving the balloon of a balloon catheter, such as the perfusion balloon catheter previously described in connection with catheter system 136 of FIG. 24. In this manner, blood may flow through orifices 156 and then through the perfusion balloon catheter to provide for sufficient blood flow during radiation therapy.

Figure 30:
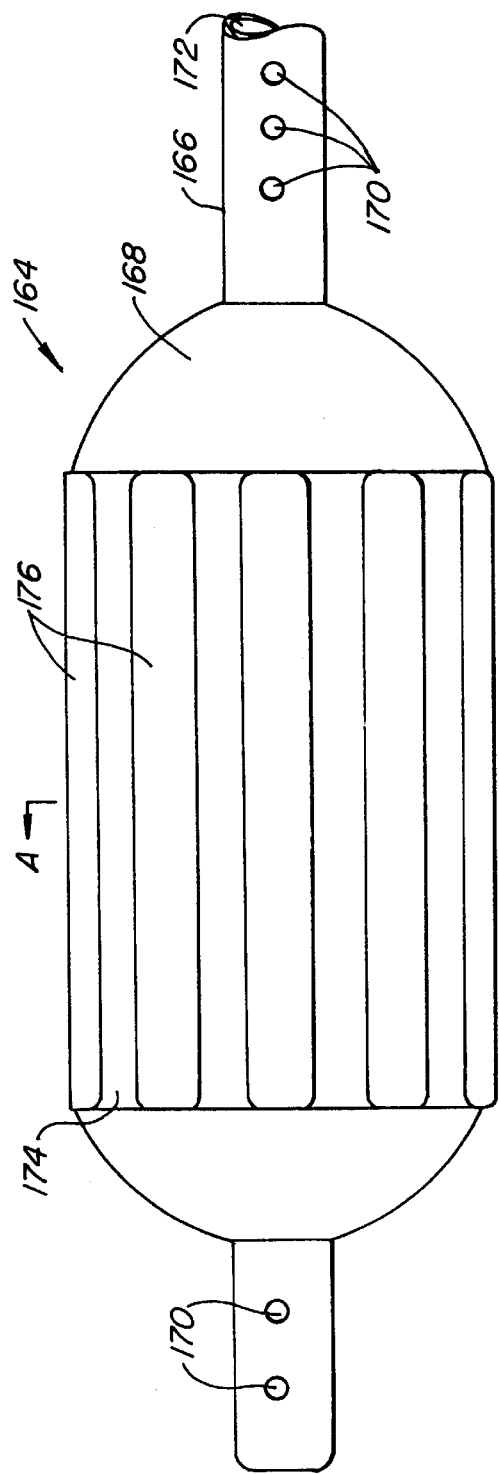
FIG. 30 is a side view of a distal end of an exemplary catheter having a plurality of radioactive elements that are secured on an elastomeric sleeve mounted over a balloon according to the present invention.
Figure 31:
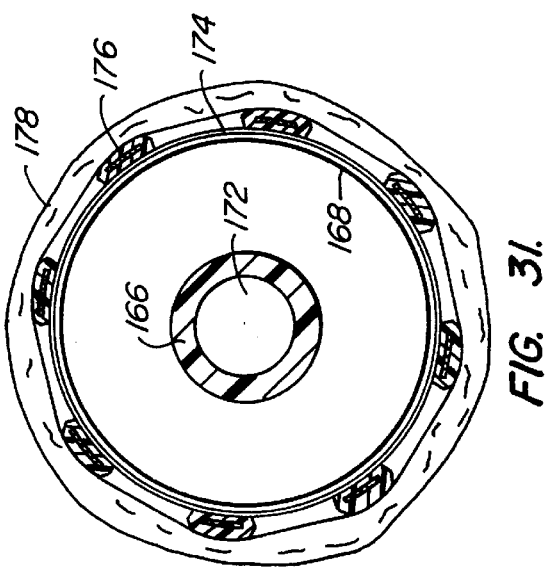
FIG. 31 is a cross-sectional view of the catheter of FIG. 30 taken along lines A—A when within a body lumen.

Another alternative embodiment of a catheter system 164 which may be employed to radioactively treat a body lumen while also providing for perfusion is illustrated in FIGS. 30 and 31. Catheter system 164 includes a balloon catheter 166 having a balloon 168. Catheter 166 includes a plurality of perfusion orifices 170 for providing blood flow through a central lumen 172 of catheter 166. Secured around balloon 168 by an elastomeric sleeve 174 are a plurality of radiation emitting elements 176. Radiation elements 176 may be constructed similar to any of the radiation elements described herein. Elastomeric sleeve 174 serves to secure radioactive elements 176 to balloon 168 and to maintain generally equal circumferential spacing between radioactive elements 176 when balloon 168 is inflated to place radioactive elements 176 in apposition to a vessel wall 178 as illustrated in FIG. 31. When balloon 168 is inflated, blood will flow through orifices 170 and through central lumen 172 to provide adequate blood flow distal to the treatment site.

Balloon 168 may comprise either an elastomeric balloon or a non-compliant balloon. Use of an elastomeric balloon is advantageous in that one size of balloon may be used to treat vessels of various sizes, while the non-compliant balloon will preferably be dedicated to a single artery size.

Figure 32:
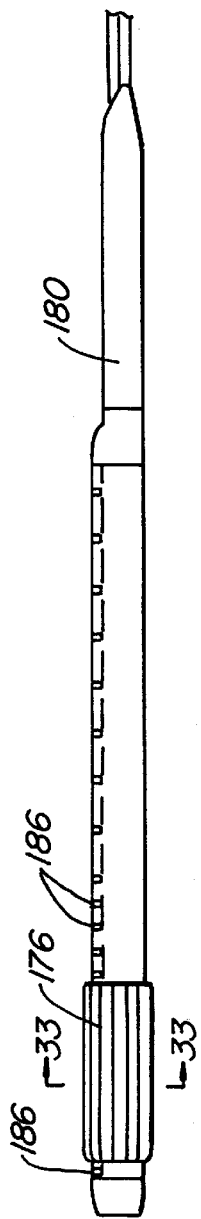
FIG. 32 is a side view of a distal end of yet another alternative embodiment of a RESC according to the present invention.
Figure 33:
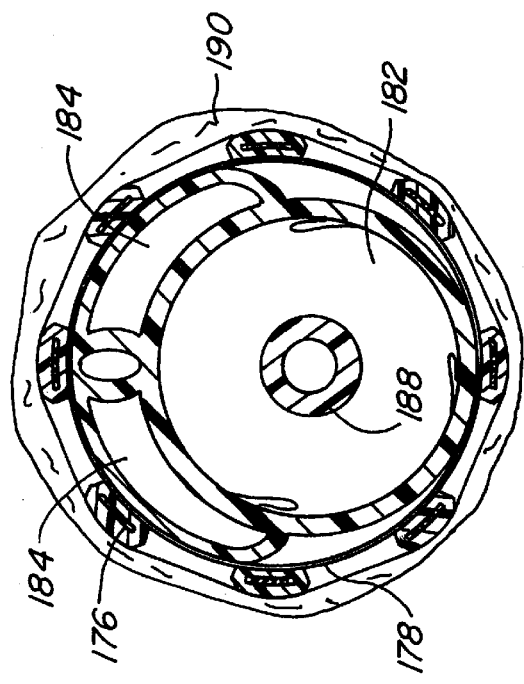
FIG. 33 is a cross-sectional view of the catheter of FIG. 32 taken along lines 33—33.

Elastomeric membrane 174 may also be employed to secure radioactive elements 176 over a perfusion catheter 180 as illustrated in FIGS. 32–33. Perfusion catheter 180 may be constructed essentially identical to the perfusion catheter described in copending application Ser. No. 08/401,541, filed Mar. 10, 1995, the complete disclosure of which is herein incorporated by reference. Perfusion catheter 180 includes a central lumen 182 and perfusion lumens 184. Blood is introduced into perfusion lumens 184 through a plurality of perfusion orifices 186. Central lumen 182 is adapted to receive a balloon catheter 188 (see FIG. 33) which in turn is employed to radially expand radioactive elements 176 to place them in apposition to a vessel wall 190. In this manner, blood may flow through orifices 186 and lumen 184 while balloon catheter 188 is inflated within the vessel.

Figure 34:
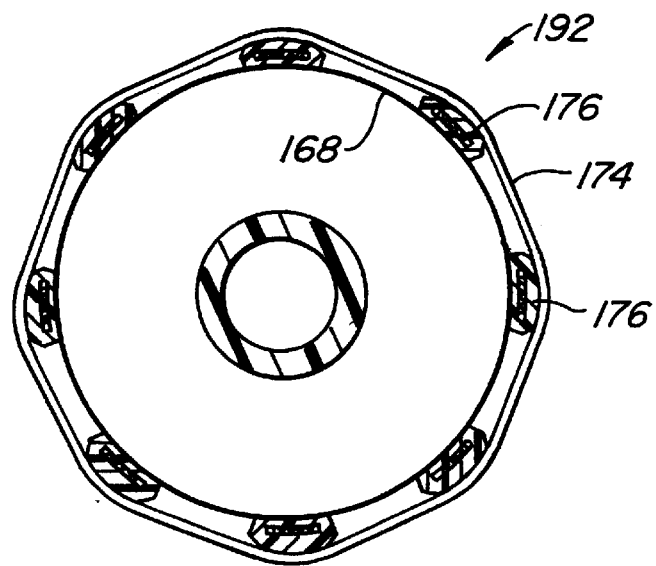
FIG. 34 is a cross-sectional end view of an alternative balloon catheter having a plurality of radioactive elements attached to the balloon and restrained by an elastomeric membrane according to the present invention.

FIG. 34 illustrates an alternative arrangement for catheter system 164 of FIG. 30. In FIG. 34, a catheter system 192 is provided which is essentially identical to that of system 164 except for the arrangement of elastomeric sleeve 174 and radioactive elements 176. In system 192, radioactive elements 176 are positioned between balloon 168 and elastomeric sleeve 174. Preferably, radioactive elements 176 will be attached to balloon 168, with sleeve 174 constraining radioactive elements 176. In this way, sleeve 174 is employed to serve as a safety device to make sure radioactive elements 176 remain attached to balloon 168 and to maintain generally equal circumferential spacing when balloon 168 is inflated as shown. Sleeve 174 further serves to collapse balloon 168 after it is deflated.

Figure 35:
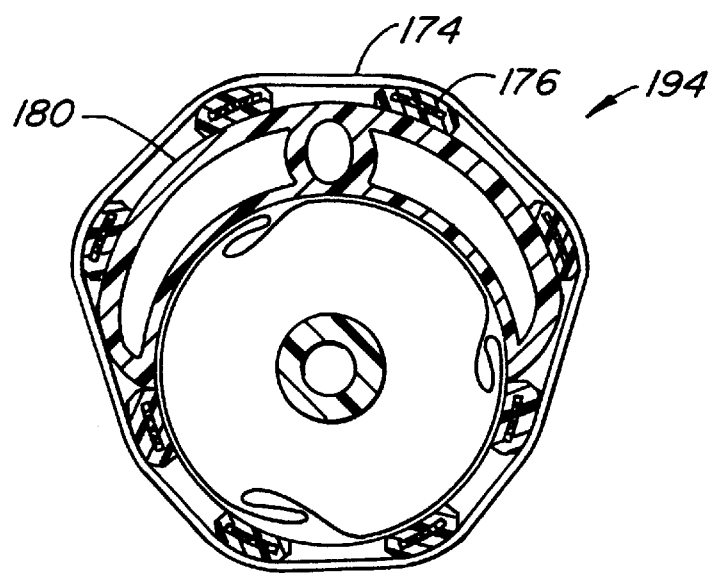
FIG. 35 is a cross-sectional end view of an alternative perfusion catheter having a plurality of radioactive elements attached thereto and restrained by an elastomeric membrane according to the present invention.

FIG. 35 illustrates an alternative embodiment of a catheter system 194 which is essentially identical to the system illustrated in FIGS. 32–33 except for the arrangement of elastomeric sleeve 174 and radioactive elements 176. In particular, radioactive elements 176 are attached to perfusion catheter 180 and elastomeric sleeve 174 is placed around radioactive elements 176. Sleeve 174 serves to maintain the attachment of the radioactive elements 176 to perfusion catheter 180 and to maintain equal circumferential spacing.

Figure 36:
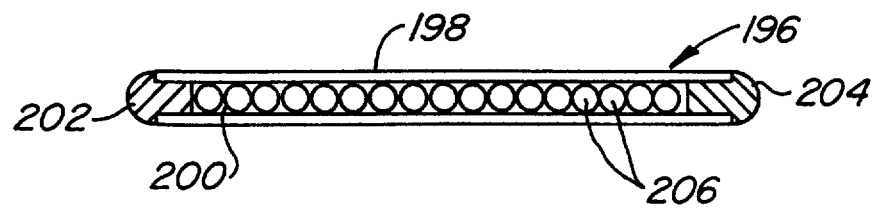
FIG. 36 is a cross-sectional side view of an exemplary seed containing a row of spherical radionuclides according to the present invention.
Figure 37:
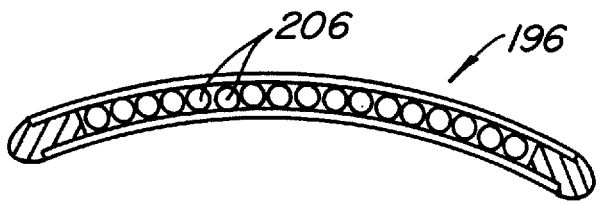
FIG. 37 illustrates the seed of FIG. 36 in a flexed configuration according to the present invention.
Figure 38:
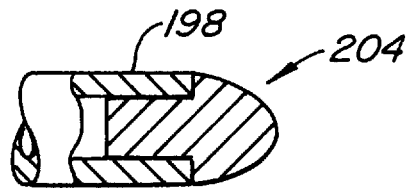
FIG. 38 is a detailed view of an end cap of the seed of FIG. 36.

Referring now to FIGS. 36–38, a preferred embodiment of a radioactive element 196 will be described. Radioactive element 196 comprises a radioactive seed and may be employed with any of the RESCs or radiation emitting catheters described herein. Radioactive element 196 comprises a generally cylindrical housing 198 having an axial lumen 200. Housing 198 has a sealed end 202 and an end plug 204 for sealing the opposite end. Held within lumen 200 are a row of generally spherical radionuclides 206.

Housing 198 will preferably have a diameter in the range from about 0.010 inch to about 0.025 inch and have a length in the range from about 15 mm to about 30 mm. In this manner, seed 196 will be small enough so that it may pass through the small arteries and vessels of the body, even when a radioactive source includes more than one seed. Another important feature of seed 196 is that it is flexible in the transverse direction (see FIG. 37) so that it may adapt to any curvature in the vessel wall when deployed. Such transverse flexibility also allows seed 196 to better navigate the tortuous vasculature during introduction and withdrawal.

Housing 198 will preferably be constructed of materials that are also able to withstand the effects of prolonged low-level radiation without substantial physical deterioration. This in turn will allow the seed 196 to be reused various times throughout its life. For example, when using radionuclides of long half-lives, e.g. $^{90}$Sr/$^{90}$Y, with a half-life of 28 years for $^{90}$Sr, an active shelf life or reusability of six months to two years may be specified. Housing 198 should remain stable and maintain its mechanical strength for longer than this specified life.

Materials which provide adequate transverse flexibility and adequate resistance to radiation include metals, such as stainless steel or nickel titanium alloy. Other suitable materials include polymers that are exceptionally resistant to the effects of radiation, including polyimides, LDPE (low density polyethylene) and the like. When constructing housing 198 of a polyimide tube, it will be preferable to also include a steel braided reinforcement therein. The steel reinforcement will help to prevent the inadvertent cutting of the polyimide housing during a procedure. Such composite tubing is commercially available from, for example, Micro-Biomedical Tubing, Inc., Cartersville, Ga., and Micro-Lumen, Inc., Tampa, Fla.

Figure 36A:
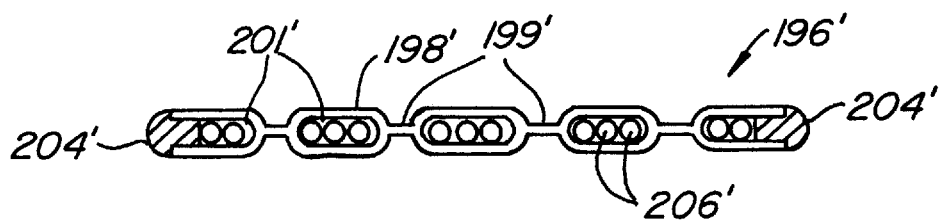
FIG. 36A is a cross-sectional side view of an alternative seed having a plurality of necked regions according to the present invention.
Figure 37A:
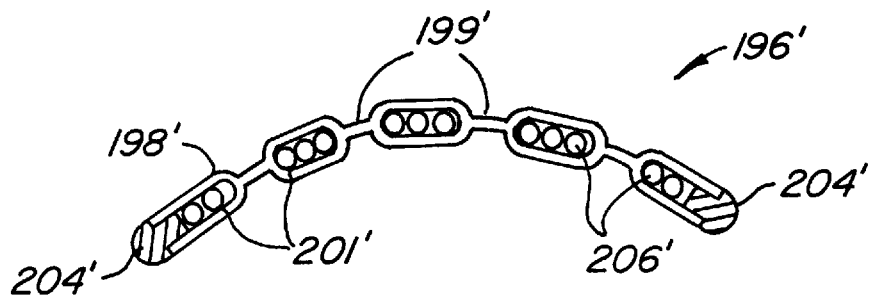
FIG. 37A illustrates the seed of FIG. 36A in a flexed configuration according to the present invention.

Illustrated in FIGS. 36A and 37A is an alternative embodiment of a seed 196'. Seed 196' is similar to seed 196 of FIGS. 36 and 37 and comprises a chain of housings 198' with the end housings sealed by end plugs 204'. A plurality of radionuclides 206' are held within housings 198'. Seed 196' differs from seed 196 in that seed 196' includes multiple necked regions 199' to divide the seed into multiple pods 201'. The necked regions 199' have a reduced cross sectional area and provide seed 196' with increased transverse flexibility as illustrated in FIG. 37A. Such improved transverse flexibility is particularly advantageous when employing multiple seeds or a single seed folded upon itself to form a cage structure in a catheter device since the traverse flexibility of the catheter will become more limited as more seeds are included.

Housings 198' may be constructed from the same materials used to construct 198. Necked regions 199' are preferably formed by deforming the housing in sequence as each pod 201' is filled with radionuclides 206'. Such methods of deformation are well known in the art. When housing 198' is constructed from nickel titanium, appropriate heat treatment will be provided in combination with the deformation process to restore the austenitic metallurgical phase of the material corresponding to its superelastic condition.

Referring to FIG. 38, construction of end plug 204 will be described in greater detail. End plug 204 will preferably be constructed so that axial lumen 200 will be completely sealed from the outside environment when end plug 204 is in place. End plug 204 may be constructed from thermoset or anaerobic adhesives that are resistant to degradation by radiation, including epoxies, cyanoacrylates, and the like. Alternatively, end plug 204 may be constructed from metals, such as stainless steel, nickel titanium, and the like and be attached to housing 198 by an epoxy or cyanoacrylate adhesive. Moreover, if housing 198 is constructed of a metallic material, and if end plug 204 is also constructed of a metallic material, end plug 204 may be staked in one or more places to firmly anchor end plug 204 to housing 198.

Seed 196 will preferably be constructed so that it is fluoroscopically visible. For example, fluoroscopic markers may be included on seed 196 (and preferably on ends 202 and 204) through the use of nickel titanium, tungsten, gold, platinum, tantalum, and the like. Further, the entire seed 196 becomes a marker if it is constructed of nickel titanium.

Radionuclides 206 will preferably comprise small spherules made from a fused ceramic matrix incorporating the radionuclide dispersed within. The radionuclide will preferably be $^{90}$Sr and $^{90}$Y which produce pure beta radiation. The $^{90}$Sr has a half-life of 28 years and the $^{90}$Sr and $^{90}$Y are in secular equilibrium. The higher energy beta radiation is produced by the $^{90}$Y. This radionuclide combination is commercially available. It is easy to shield and even when unshielded presents a low irradiation exposure for the patient and cath lab staff alike.

As previously described in connection with FIG. 18, as the radiation dose is measured deeper into the vessel, the dose uniformity rapidly improves. Hence, in some cases it will be desirable to place an energy attenuator between the vessel wall and the radioactive source so that a generally uniform circumferential dose distribution can be provided at the vessel wall. Such an energy attenuator will preferably comprise a material which is denser than the vessel wall, blood, or other material within the vessel. Exemplary materials for providing such attenuation include stainless steel, nickel titanium alloys and the like.

Figure 39:
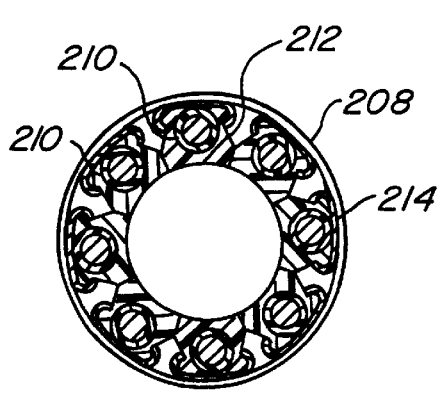
FIG. 39 is a cross-sectional end view of still a further alternative embodiment of a RESC having radioactive seeds according to the present invention.
Figure 40:
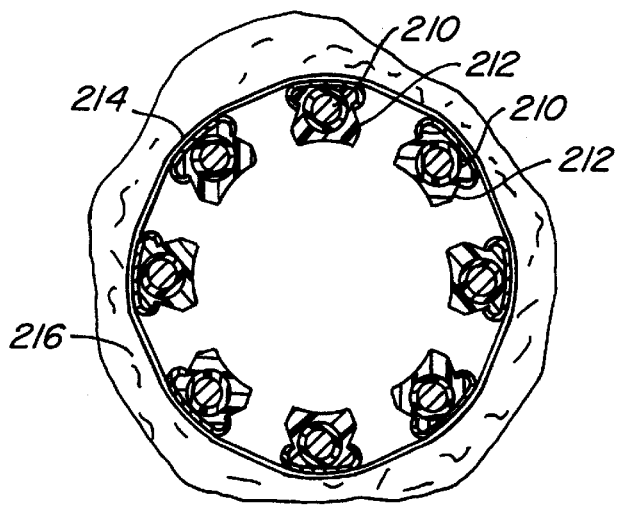
FIG. 40 illustrates the RESC of FIG. 39 when radially expanded.
Figure 41:
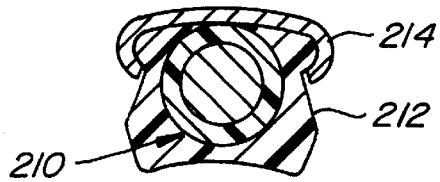
FIG. 41 is a more detailed view of one of the seeds of the RESC of FIG. 39 contained within a polymeric channel that is sealed with a clip according to the present invention.

Referring now to FIGS. 39–41, an exemplary RESC 208 which is useful in providing an improved uniform circumferential radiation dose distribution will be described. For convenience of discussion, only a distal portion of RESC 208 will be described, it being understood that the body of the catheter may be constructed in accordance with the principles of other embodiments described herein. RESC 208 includes a plurality of seeds 210 which may be constructed essentially identical to seeds 196 as previously described. Seeds 210 are held within a containment channel 212 which is preferably constructed of an LDPE extrusion. Seed 210 is sealed within channel 212 with an attenuator/seal 214 which comprises a superelastic nickel titanium clip. Seal 214 securely seals seed 210 within channel 212 and also provides protection to seed 210 so that a scalpel or other surgical instrument will not inadvertently cut into seed 210.

As shown in FIG. 40, when RESC 208 is radially expanded within an artery 216, attenuators 214 are placed in apposition to the artery wall. By attenuating the energy from seeds 210, attenuators 214 are able to provide a more uniform circumferential radiation dose distribution at the artery wall. As with other embodiments described herein, RESC 208 will preferably be stored within vacuum packaging or nitrogen-filled packaging to inhibit polymer degradation, which is greater in the presence of oxygen.

Figure 42:
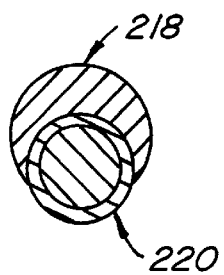
FIG. 42 is a cross-sectional end view of an eccentric attenuator cap for attenuating energy emitted from a radioactive seed according to the present invention.

Referring to FIG. 42, an alternative embodiment of an attenuator 218 will be described. Attenuator 218 comprises an eccentric cap which is typically constructed of a nickel titanium alloy. Attenuator 218 is placed over a portion of a seed 220 which may be essentially identical to the seeds previously described herein.

Figure 43:
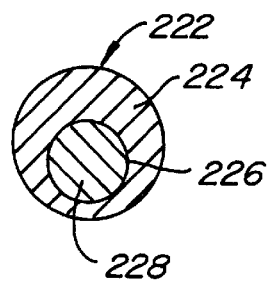
FIG. 43 is a cross-sectional end view of a seed housing having an eccentric lumen according to the present invention.

Another alternative embodiment of an attenuator 222 is shown in FIG. 43. The attenuator is formed by constructing a seed 224 of a tube with an eccentric lumen 226 which holds a row of spherical radionuclides 228. In this configuration, the housing and attenuator are combined into a single seed 224. Seed 224 will preferably be constructed of a nickel titanium alloy, with the thickest portion being employed as the attenuator. In this way, radioactive energy from radionuclides 228 will be best attenuated by the thickest portion of attenuator 222 which is placed on the RESC or balloon so that it will come into apposition with the vessel wall.

The invention further provides exemplary catheter systems which may employ seeds such as those previously described in connection with FIG. 36. One such catheter system 230 is illustrated in FIGS. 44 and 45. System 230 comprises a catheter 232 (only a distal end of which is shown) having a catheter body 234 and an elastomeric balloon 236. Included within catheter body 234 is a guidewire lumen 238 housing a guidewire 240. Guidewire lumen 238 may exit on a side of the catheter body 234 proximal of balloon 236 as shown in FIG. 45 or may alternatively extend to a proximal end of the catheter body. In this manner, catheter 232 may be used in either a "rapid exchange" mode or an over-the-wire mode.

Catheter 232 further includes an inflation lumen 242 for inflating elastomeric balloon 236. A plurality of seeds 244 are embedded within elastomeric balloon 236. Seeds 244 may be essentially identical to seeds 196 of FIG. 36. Elastomeric balloon 236 will be preferably constructed of a material that is able to withstand a low level of radiation over an extended period of time without substantial degradation as previously described in connection with FIG. 22. Radial expansion of elastomeric balloon 236 is further illustrated in FIGS. 46 and 47. As shown in FIG. 46, balloon 236 is in a deflated position, such as when being introduced to a body lumen. When radially expanded with a fluid, balloon 236 is deployed radially outward as illustrated in FIG. 47 to place seeds 244 in apposition to a vessel wall.

Figure 48:
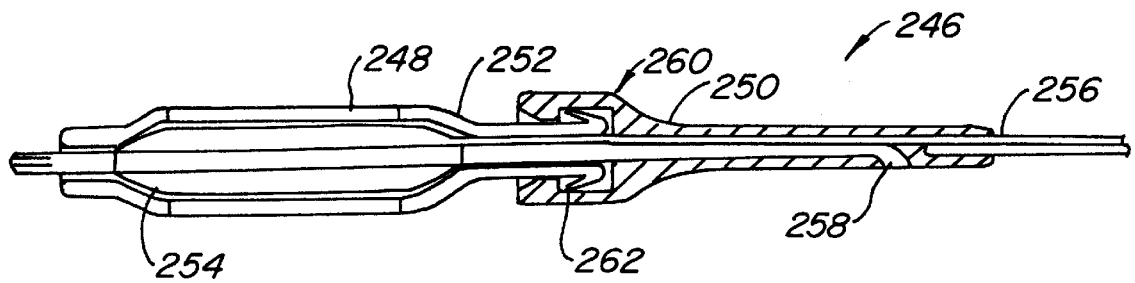
FIG. 48 is a cross-sectional side view of an exemplary catheter having an attachable head which includes a plurality of radioactive members according to the present invention.

An alternative embodiment of a catheter system 246 having seeds 248 is illustrated in FIG. 48. System 246 includes a catheter body 250 and a separate head 252. Catheter body 250 further includes a balloon 254, a balloon inflation lumen 256, and a guidewire lumen 258. Catheter body 250 also includes a locking mechanism 260 into which prongs 262 of head 252 are received. In this manner, head 252 (which includes seeds 248) may be fixedly secured to catheter body 250 by inserting prongs 262 into locking mechanism 260. When locked in place, seeds 248 will be aligned over balloon 254 so that balloon 254 may be inflated to place seeds 248 in apposition to a vessel wall. Seeds 248 may be held within axial slits (such as shown in connection with FIG. 16), within a folded membrane (such as shown in FIGS. 9 and 10), or embedded within an elastic membrane (such as shown in FIGS. 46 and 47). One particular advantage of providing a separate head 252 is that the head with the seeds 248, rather than the entire catheter, may be conveniently held within a shielded docking module until ready for introduction into the patient as described in greater detail hereinafter.

Figure 49:
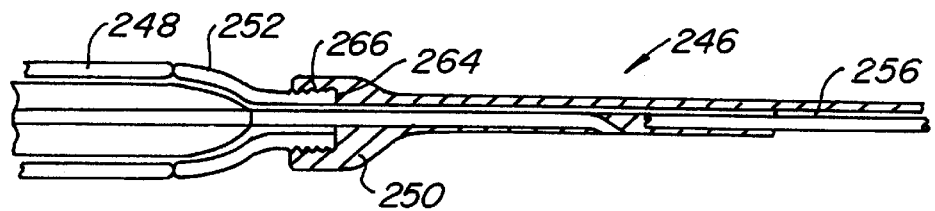
FIG. 49 is a cross-sectional side view of an alternative catheter having an attachable head according to the present invention.

An alternative locking mechanism for catheter system 246 is illustrated in FIG. 49. To fixedly attach head 252 to catheter body 250, catheter body is provided with a threaded joint 264 for receiving a threaded end 266 of head 252.

Figure 50:
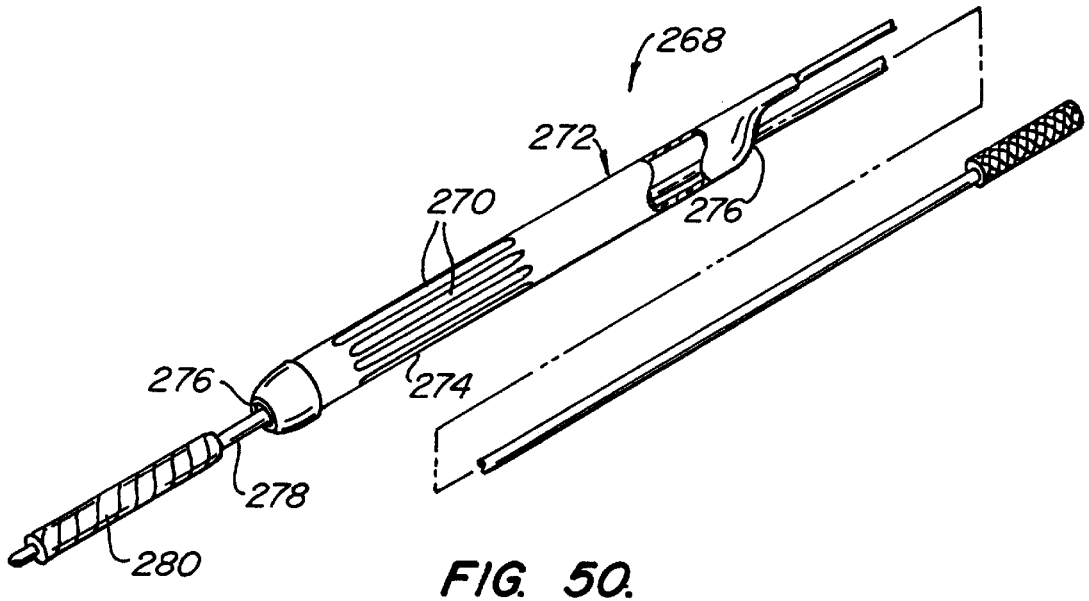
FIG. 50 illustrates a further alternative embodiment of a RESC which includes a plurality of radioactive seeds according to the present invention.

Still another embodiment of a catheter system 268 for introducing seeds 270 to a treatment region is illustrated in FIG. 50. System 268 comprises a catheter sleeve 272 which may be constructed similar to the stent delivery catheter described in copending U.S. application Ser. No. 60/002, 847, filed Sep. 27, 1996 (Attorney Docket Number 15509-002800), the disclosure of which is herein incorporated by reference. Catheter sleeve 272 includes a radially deployable region 274 in which seeds 270 are held. Radially deployable region may include elongate slits, a folded membrane, an elastomeric membrane or an offset slitting pattern as previously described. Catheter sleeve 272 includes a central lumen 276 into which a balloon catheter 278 having a balloon 280 is received. In this manner, balloon 280 may be inflated to radially deploy seeds 270 into apposition with a vessel wall.

Referring now to FIGS. 51 and 52, an exemplary shielded docking module 282 will be described. Docking module 282 is provided to enable the safe shipping of the radioactive catheter systems described herein. Docking module 282 also protects both cath lab personnel and the patient from beta radiation emitting from the radionuclides and from Bremsstrahlung emitting from the shielding surrounding the catheter head. Although useful with essentially all the catheter systems described herein, docking module 282 will be particularly useful in storing head 252 of catheter system 246.

Docking module 282 comprises a cylindrical housing made of quartz or acrylic polymer (plexiglass) and has a wall thickness in the range from about 0.5 cm to about 2 cm. Housing 284 in turn is surrounded by a lead casing 286 to absorb the Bremsstrahlung generated in the quartz or acrylic shield. The cross-section of docking module 282 having a catheter sleeve or catheter head 288 therein is shown in FIG. 52. Optionally, as shown in FIG. 51, housing 284 may further incorporate a female luer lock 290 for attachment to a male luer lock of a guide catheter. A safety release 292 may also optionally be provided to insure that the catheter or catheter head may not be pushed out of the shield portion accidentally.

Referring to FIG. 53, a further alternative embodiment of a radioactive source 300 will be described. Radioactive source 300 comprises a single elongate, flexible self supporting seed 302 which may be constructed similar to seed 196 of FIG. 36. Seed 302 includes a proximal end 304 and a distal end 306, and is folded into five strands to form an expansible cage structure. Folding seed 302 into an odd number of strands is advantageous in that radiopaque end plugs 308 and 310 may be placed at proximal end 304 and distal end 306 to help locate seed 302 fluoroscopically. Another advantage of seed 302 is that it is reusable. Optionally, seed 302 may be attached to a push rod 311 for ease of manipulation similar to the catheter described in copending application Ser. No. 08/08,551,932, previously incorporated by reference.

Similar to seed 196, seed 302 may be constructed of a superelastic material, such as a Nickel Titanium tubing, and will preferably be formed into a collapsed configuration. Following radial expansion, seed 302 will then collapse by itself after the internal pressure is removed. The pitch of seed 302 will preferably be long enough so that it may be able to navigate through a tortuous vasculature and adapt to a curved vessel when expanded.

Seeds such as seed 302 may also be incorporated into both balloon attachment embodiments and sleeve attachment embodiments. For example, seed 302 may be embedded within an elastomeric balloon similar to the embodiment of FIG. 44. Seed 302 may also be included within a radially expansive sleeve which is slid over a balloon. Seed 302 may optionally include an internal or an external elastomeric membrane as shown in FIGS. 11, 32, 34 and 35.

Seed 302 may be configured to be shorter than a balloon 312 as illustrated in FIGS. 54A and 54B. In this manner, when balloon is inflated as shown in FIG. 54B, a longitudinal dose distribution similar to that shown in FIG. 55 will be produced. Alternatively, seed 302 may be configured to be longer than balloon 312 as illustrated in FIGS. 56A and 56B. Due to the deviation from a cylindrical shape, such a configuration is likely to produce a longitudinal dose distribution with a gentler proximal and distal slope as shown in FIG. 57. This also makes alignment between the seed 302 and the lesion less critical.

Figure 58:
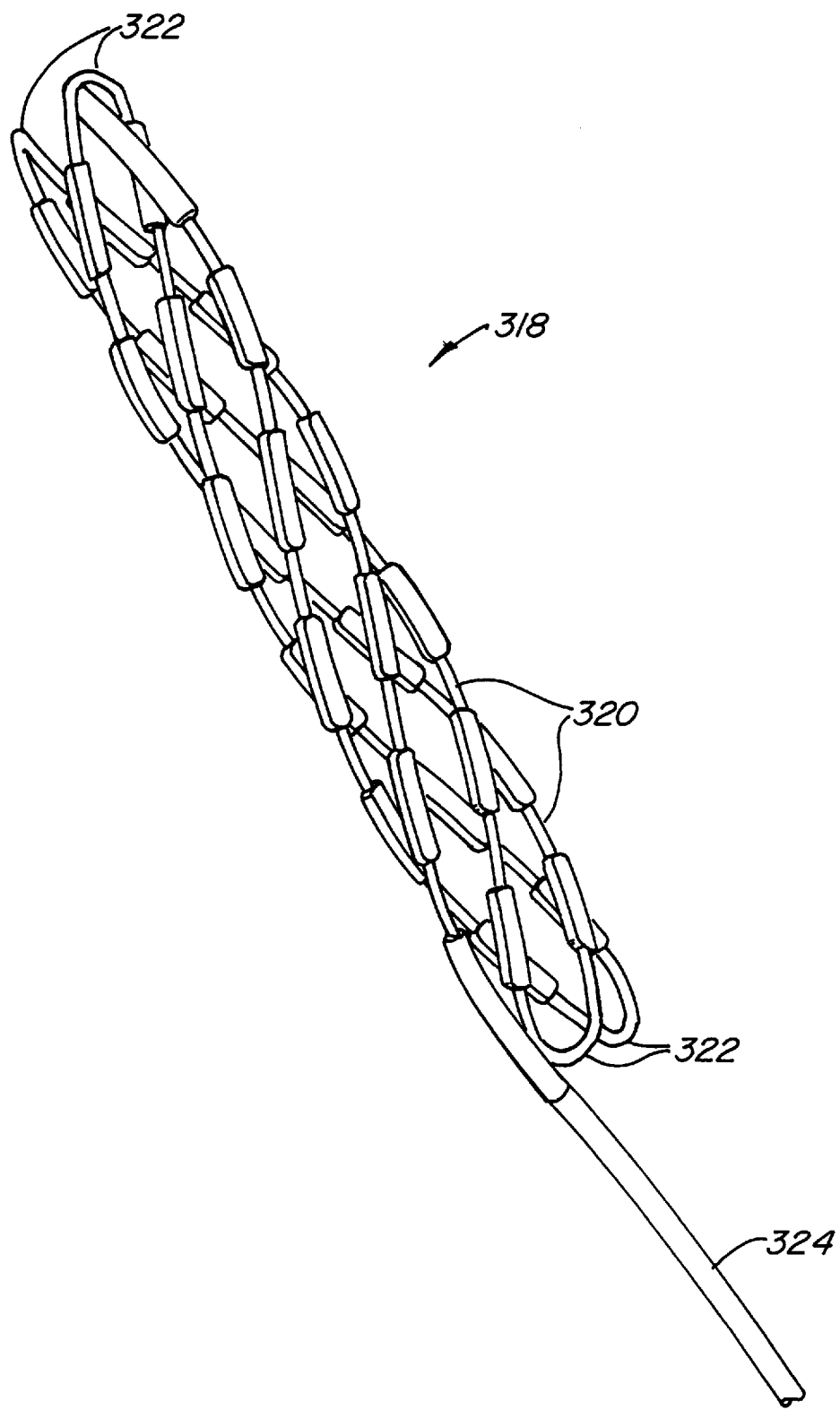
FIG. 58 illustrates an alternative embodiment of a self supporting single seed folded into an expansible cage structure according to the present invention.

Referring now to FIG. 58, an alternative embodiment of a self supporting seed 318 will be described. Seed 318 is essentially identical to seed 302 except that seed 318 includes multiple necked regions 320 and 322. Necked regions 320 provide seed 318 with increased transverse flexibility similar to seed 196' of FIGS. 36A and 37A. Necked regions 322 are also placed in the major bends of the seed and are provided to facilitate the expansion of the seed from its collapsed into its expanded configuration. Seed 318 may be employed to treat a body lumen using methods similar to those described in connection with seed 302 and may optionally include a push rod 324 to facilitate manipulation.

Although the foregoing invention has been described in some detail by way of illustration and example, for purposes of clarity of understanding, it will be obvious that certain changes and modifications may be practiced within the scope of the appended claims.

What is claimed is:

1. A catheter system comprising:
   an elongate catheter body having a proximal end and a distal end;
   at least one radioactive element operably attached to the catheter body near the distal end;
   an expansible member which radially expands the radioactive element away from the catheter body and toward a vessel wall; and
   an energy attenuator disposed about at least a portion of the radioactive element so as to produce a generally uniform circumferential radiation dose distribution having a lesser radial energy gradient at the vessel wall upon expansion of the expansible member.

2. A catheter system as in claim 1, wherein the radioactive element comprises a seed, and wherein the seed comprises a housing and an arrangement of radionuclides contained within the housing.

3. A catheter system as in claim 2, wherein the radionuclides are spherical in geometry and are arranged in a row within the housing.

4. A catheter system as in claim 2, wherein the housing includes at least one necked region having a reduced cross sectional area to increase the transverse flexibility of the seed.

5. A catheter system as in claim 2, wherein the seed is uniformly distributed about the periphery of the catheter body.

6. A catheter system as in claim 2, wherein the seed housing comprises a radiation resistant polymer reinforced with a flexible stainless steel braiding, and wherein the housing is flexible in the transverse direction.

7. A catheter system as in claim 2, wherein the seed housing is constructed of a material displaying superelastic properties, and wherein the housing is flexible in the transverse direction.

8. A catheter system as in claim 7, wherein the housing includes at least one necked region having a reduced cross sectional area to increase the transverse flexibility of the seed.

9. A catheter system as in claim 1, further comprising at least one fluoroscopic marker disposed at a known position relative to the catheter body so that the catheter is visible fluoroscopically within a body lumen.

10. A catheter system as in claim 2, wherein the housing is constructed at least partially of nickel titanium to make the housing fluoroscopically visible.

11. A catheter system as in claim 2, further comprising end caps for enclosing and sealing the seed.

12. A catheter system as in claim 11, wherein the seed housing and the end caps are constructed of a metallic material, and wherein the end caps and the housing are staked together.

13. A catheter system as in claim 11, wherein the end caps and the housing are welded together.

14. A catheter system as in claim 2, wherein the seed housing is constructed of a material displaying superelastic properties and includes an eccentric lumen for holding the radionuclides, the eccentric lumen forming an arcuate thick wall portion and an arcuate thin wall portion of the housing, and wherein the attenuator comprises the thick wall portion of the housing.

15. A catheter system as in claim 2, wherein the seed is cylindrical in geometry, and wherein the attenuator comprises an arcuate eccentric cap positioned around at least a portion of the seed.

16. A catheter system as in claim 2, wherein the seed is housed within a radiation resistant polymeric channel, and wherein the attenuator comprises a nickel titanium clip which captures the seed within the channel.

17. A catheter system as in claim 2, wherein the seed is operably attached to the radially expansible member.

18. A catheter system as in claim 17, wherein the radially expansible member comprises an elastomeric balloon, and wherein the seed is embedded within a wall of the balloon.

19. A catheter system as in claim 2, further comprising a sleeve which is slidable over the catheter body, and wherein the seed is included in the sleeve.

20. A catheter system as in claim 19, wherein the sleeve comprises a flexible material which is folded until deployed by the radially expansible member.

21. A catheter system as in claim 19, wherein the sleeve comprises an elastomeric material.

22. A catheter system as in claim 19, wherein the sleeve includes a plurality of slits, and wherein the seed is aligned on the sleeve in the direction of the slits.

23. A catheter system as in claim 2, wherein the radionuclides include $^{90}$Strontium and $^{90}$Yttrium.

24. A catheter system as in claim 1, wherein the catheter body further comprises a removable head, and wherein the radioactive element is operably attached to the head.

25. A catheter system as in claim 2, wherein the seed includes a fluoroscopically visible marker which is constructed at least partially of a fluoroscopically visible material selected from the group consisting of nickel titanium, tungsten, gold, platinum, and tantalum.

26. A catheter system as in claim 1, further comprising a plurality of radioactive elements operably attached to the catheter body.

27. A catheter system as in claim 2, wherein the seed is folded into an expansible cage structure.

28. A catheter system as in claim 27, wherein the housing includes at least one necked region having a reduced cross sectional area to increase the transverse flexibility of the seed.

29. A catheter system as in claim 27, wherein the seed is longer than the expansible member.

30. A method for providing radiation therapy to a patient, the method comprising:
performing angioplasty on a coronary artery to produce a treatment region;
introducing a catheter to the treatment region, the catheter comprising a catheter body having a proximal end and a distal end, at least one radioactive element operably attached to the catheter body near the distal end and a balloon; and
inflating the balloon when at the treatment region to radially move the radioactive element toward the artery so that the radioactive element is spaced apart from the artery wall by a predetermined distance in the range from about 0.25 mm to about 0.5 mm;
wherein the irradiation energy from the radiation emitting element is attenuated when travelling outward so as to provide a generally uniform circumferential radiation treatment. to the treatment region.

31. A method as in claim 30, wherein the balloon is constructed of an elastomeric material, and wherein the radioactive element is formed within the balloon.

32. A method as in claim 30, further comprising a sleeve which is slidable over the catheter body, wherein the radioactive element is housed in the sleeve, and further comprising placing the sleeve over the balloon before inflating the balloon.

33. A method as in claim 32, wherein the sleeve comprises a flexible material which is folded until deployed by the radially expansible member.

34. A catheter as in claim 32, wherein the sleeve includes a plurality of slits, and wherein the seed is aligned on the sleeve in the direction of the slits.

35. A method as in claim 30, wherein the catheter further comprises an attachable head, wherein the radioactive elements are operably attached to the head, and further comprising attaching the head to the catheter body prior to introducing the catheter to the treatment region.

36. A method as in claim 30, further comprising introducing at least some beta radiation to the treatment region with the radioactive element.

37. A method as in claim 30, further comprising maintaining the catheter at the treatment region for a period of time not exceeding about three minutes.

38. A method as in claim 30, wherein the radioactive element comprises a seed, and further comprising removing the seed from the catheter after treating the treatment region and reusing the seed on another catheter.

39. A method as in claim 38, wherein the seed is folded into an expansible cage structure.

40. A method as in claim 39, wherein the seed is longer than the balloon.

41. A catheter system, comprising:
an elongate catheter body having a proximal end, a distal end and a longitudinal axis;
a head having an attachment mechanism for fixedly attaching the head to the distal end of the catheter body such that the head is disposed distally of the catheter body and is generally aligned with the longitudinal axis;
at least one radioactive element operably attached to the head; and
an expansible member operably attached to the catheter body which radially expands the radioactive element away from longitudinal axis of the catheter body.

42. A system as in claim 41, wherein the attachment mechanism includes a lock which locks the head to the catheter body.

43. A system as in claim 41, wherein the catheter body includes an inflation lumen and a guidewire lumen.

44. A system as in claim 43, wherein the guidewire lumen proximally terminates in a guidewire exit port on a side of the catheter body.

45. A system as in claim 43, wherein the guidewire lumen terminates at a proximal catheter fitting at the proximal end of the catheter body.

46. A system as in claim 41, further comprising an energy attenuator which is disposed about at least a portion of the radioactive element so as to produce a generally uniform circumferential radiation dose distribution at a vessel wall.

47. A system as in claim 41, further comprising a docking module defining an enclosure for housing the head, the docking module absorbing the release of radioactive energy from the radioactive element.

48. A system as in claim 41, further comprising a packaging enclosure, wherein the head is vacuum or nitrogen packed within the packaging enclosure.

49. A system as in claim 41, wherein the radioactive element comprise a seed, the seed comprising a housing and a plurality of radionuclides contained within the housing.

50. A system as in claim 49, wherein the housing includes at least one necked region having a reduced cross sectional area to increase the transverse flexibility of the seed.

51. A system as in claim 49, wherein the seed is uniformly distributed about the periphery of the head.

52. A system as in claim 49, wherein the seed housing comprises a radiation resistant polymer reinforced with a flexible stainless steel braiding, and wherein the housing is flexible in the transverse direction.

53. A system as in claim 49, wherein the seed housing is constructed of a material displaying superelastic properties, and wherein the housing is flexible in the transverse direction.

54. A system as in claim 53, wherein the housing includes at least one necked region having a reduced cross sectional area to increase the transverse flexibility of the seed.

55. A system as in claim 49, wherein the seed includes end caps which are insertable into ends of the seed housing to seal the seed.

56. A method for providing radiation therapy to a patient, the method comprising:
performing angioplasty on a body lumen to produce a treatment region;
providing a catheter comprising an elongate catheter body having a proximal end, a distal end, a longitudinal axis, a head adapted for attachment to the distal end of the catheter body such that the head is disposed distally of the catheter body and is generally aligned with the longitudinal axis, at least one radioactive elements operably attached to the head, and an expansible member operably attached to the head, with the head being aligned with the longitudinal axis;
fixedly attaching the head to the catheter body;
introducing the catheter to the treatment region;
inflating the balloon when at the treatment region to move the radioactive element towards the body lumen.

57. A method as in claim 56, further comprising attaching the head to the catheter body while the head is disposed within a radioactive shield.

58. A method as in claim 56, further comprising attenuating the energy from the radiation emitting element with an attenuator so as to provide a generally uniform circumferential radiation treatment to the treatment region.

59. A method as in claim 56, further comprising inflating the balloon until the balloon moves the radioactive element to a predetermined distance from the artery wall.

60. A method as in claim 56, wherein the radioactive element comprise a seed, and further comprising removing the seed from the catheter after treating the treatment region and reusing the seed on another catheter.

61. A catheter comprising:
   an elongate catheter body having a proximal end and a distal end;
   a radially expansible member near the distal end;
   a radially expansible sleeve which is positionable over the expansible member to allow the sleeve to be radially expanded by the expansible member; and
   a plurality of seeds operably attached to the sleeve, each seed comprising an elongate flexible housing having an axial lumen and a plurality of radionuclides, and wherein a row of the radionuclides is housed within each lumen.

62. A catheter as in claim 61, wherein the seed is folded into an expansible cage structure.

63. A catheter as in claim 61, wherein the radionuclides are spherical in geometry.

64. A catheter as in claim 60, wherein the radially expansible member comprises an elastomeric balloon.

65. A catheter as in claim 60, wherein the seeds are uniformly distributed about the balloon.

66. A catheter as in claim 61, wherein the flexible housing comprises a radiation resistant polymer reinforced with a flexible stainless steel braiding.

67. A catheter as in claim 61, wherein the flexible housing is constructed of a material displaying superelastic properties.

68. A catheter as in claim 67, wherein the material displaying superelastic properties comprises nickel titanium.

69. A catheter as in claim 61, wherein the seed includes end caps for enclosing ends of the seed housing.

70. A catheter as in claim 69, wherein the end caps are constructed of a non-metallic material selected from the group consisting of cyanoacrylates and epoxy.

71. A catheter as in claim 69, wherein the end caps are constructed of a metallic material and are attached to the housing by cyanoacrylates or epoxies.

72. A catheter as in claim 61, wherein the radionuclides include $^{90}$Strontium and $^{90}$Yttrium.

73. A catheter as in claim 72, wherein the radionuclides further include a ceramic material.

74. A catheter comprising:
   an elongate catheter body having a proximal end and a distal end;
   an elastomeric balloon near the distal end of the catheter body; and
   at least one radioactive element integrally formed within the elastomeric balloon such that the radioactive element is evenly circumferentially spaced about the balloon when expanded.

75. A catheter as in claim 74, further comprising a plurality of radioactive elements integrally formed within the balloon.

76. A catheter as in claim 74, wherein the radioactive element comprises a seed, the seed comprising an elongate flexible housing having an axial lumen and a row of radionuclides within the lumen, and wherein the seed is integrally formed within the balloon.

77. A catheter as in claim 76, wherein the seed is folded into an expansible cage structure.

78. A catheter system comprising:
   a catheter comprising a catheter body having a proximal end, a distal end, and a longitudinal axis;
   a head having an attachment mechanism for fixedly attaching the head to the distal end of the catheter body such that the head is disposed distally of the catheter body and is generally aligned with the longitudinal axis;
   an elastomeric balloon operably attached to the head of the catheter body; and
   a plurality of seeds, each seed comprising an elongate flexible housing having an axial lumen and a plurality of radionuclides within the lumen;
   wherein the seeds are integrally formed within the elastomeric balloon such that the seeds are evenly circumferentially spaced about the balloon when expanded.

79. A catheter system as in claim 78, further comprising a docking module defining an enclosure for housing the head and the balloon, the docking module absorbing the release of energy from the seeds.

80. A method for providing radiation therapy to a patient, the method comprising:
   performing angioplasty on a body lumen to produce a treatment region;
   introducing a catheter system to the treatment region, the catheter system comprising a catheter having a catheter body defining a central lumen, a balloon, and a sleeve having an expansible region and a plurality of radioactive elements which are generally disposed over and aligned with the balloon;
   inflating the balloon when at the treatment region; and
   introducing a radioactive member through the central lumen so that the radioactive member is axially aligned with the radioactive elements of the sleeve to provide a generally uniform circumferential radiation dose to the treatment region.

81. A method as in claim 80, wherein the radioactive elements of the sleeve are generally evenly distributed around the circumference of the balloon when inflated.

82. A method as in claim 80, wherein the catheter is introduced over a first guide wire, and further comprising removing the first guide wire after inflating the balloon, and introducing a second guide wire having the radioactive member.

83. A method as in claim 82, further comprising fluoroscopically visualizing the catheter and the second guide wire when introducing the catheter to the treatment region to align the radioactive elements and the radioactive member with the treatment region.

84. A method as in claim 80, wherein the radioactive elements and the radioactive member emit at least some beta radiation, and further comprising maintaining the combined catheter and sleeve at the treatment region for a time in the range from about 1 min to about 3 min to achieve a dose of from about 5 Gy to about 50 Gy at a luminal surface of the body lumen.

85. A radiation emitting catheter system, comprising:
   an elongate catheter body having a proximal end, a distal end and a central lumen;

an elastomeric balloon attached near the distal end of the catheter body;

at least one radiation emitting element attached to the elastomeric balloon; and a guide wire which is receivable in the central lumen.

86. A system as in claim 85, wherein the guide wire includes a radiation emitting source, the guide wire being adapted to be received in the central lumen with the radiation emitting source being surrounded by the radiation emitting element on the balloon so as to produce a generally uniform circumferential radiation dose distribution.

87. A system as in claim 85, further comprising a plurality of radiation emitting elements, wherein the radiation emitting elements are disposed within polymeric housings, and wherein the housings are evenly distributed about the periphery of the balloon, whereby the radiation emitting elements are evenly circumferentially spaced when the balloon is inflated.

88. A system as in claim 85, wherein the radioactive element comprises a seed, and wherein the seed comprises a housing and a row of radionuclides contained within the housing.

89. A system as in claim 85, wherein the balloon is constructed of materials selected from the group consisting of polyurethane, natural rubbers and synthetic rubbers, wherein the catheter body centers the radiation emitting source within the balloon.

90. A method for performing angioplasty, the method comprising:

introducing an angioplasty catheter having an angioplasty balloon to a body lumen and inflating the angioplasty balloon to produce a treatment region;

removing the angioplasty catheter from the patient;

introducing a radiation emitting catheter having a central lumen, an elastomeric balloon and a plurality of radiation emitting elements around the elastomeric balloon to the treatment region and inflating the elastomeric balloon to provide radiation treatment to the treatment region.

91. A method as in claim 90, further comprising introducing a radioactive source through the central lumen so that the radioactive source is axially aligned with the radioactive elements on the elastomeric balloon.

92. A method as in claim 90, wherein the radioactive elements on the elastomeric balloon are evenly distributed around the circumference of the elastomeric balloon when inflated.

93. A method as in claim 91, wherein the angioplasty catheter is introduced over a first guide wire, and further comprising removing the angioplasty balloon after inflating the angioplasty balloon, introducing the radiation emitting catheter over the first guide wire, removing the first guide wire, and introducing a second guide wire having the radioactive source.

94. A method as in claim 93, further comprising fluoroscopically visualizing the radiation emitting catheter and the second guide wire when introducing the radiation emitting catheter and the second guide wire to the treatment region to align the radioactive elements and the radioactive member with the treatment region.

95. A method as in claim 91, wherein the radioactive elements and the radioactive source emit at least some beta radiation, and further comprising maintaining the combined radiation emitting catheter at the treatment region for a time in the range from about 1 min to about 3 min.

96. A method as in claim 91, wherein the elastomeric balloon is filled with a predetermined volume of fluid to inflate the balloon to a known size, and wherein the inflated elastomeric balloon centers the radiation emitting source within the body lumen.

97. A catheter system comprising:

a balloon catheter having a catheter body with a proximal end, a distal end, a lumen extending therebetween, and a balloon disposed near the distal end;

a sleeve having a radially expansible and contractible region, wherein at least one radioactive element is evenly distributed about the expansible region; and wherein the catheter body includes orifices proximal and distal to the balloon for allowing blood to pass by the balloon through the lumen.

98. A catheter system as in claim 97, wherein the sleeve includes orifices proximal to the radially expansible region to allow blood to flow through the sleeve and to the proximal catheter body orifices.

99. A catheter system as in claim 98, wherein the sleeve includes axial slits, and wherein the radioactive element is aligned with the slits.

100. A catheter system as in claim 98, wherein the sleeve is configured to have an offset slitting pattern.

101. A catheter system as in claim 97, wherein the sleeve comprises an elastomeric material which is disposed about the balloon, and wherein the radioactive element is attached to an outer surface of the sleeve.

102. A catheter system as in claim 97, wherein the sleeve comprises an elastomeric material which is disposed about the balloon, and wherein the radioactive element is held between an inner surface of the sleeve and the balloon.

103. A catheter system as in claim 97, wherein the sleeve comprises an elastomeric material and wherein the radioactive element is embedded within the sleeve.

104. A catheter system as in claim 97, further comprising an elongate rod attached to a proximal end of the sleeve.

105. A method for providing radiation therapy to a patient, the method comprising:

performing angioplasty on a body lumen to produce a treatment region;

introducing a catheter to the treatment region, the catheter comprising a catheter body having a central lumen, a balloon, and a sleeve having an expansible and contractible region disposed over the balloon, wherein the sleeve includes at least one radioactive elements distributed about the sleeve so as to be axially aligned with the balloon, and wherein the catheter body includes perfusion orifices proximal to the balloon; and aligning the balloon and the sleeve with the treatment region and inflating the balloon, wherein blood is allowed to flow through the treatment region of the coronary artery by passing through the perfusion orifices and the central lumen.

106. A method as in claim 105, wherein the sleeve includes orifices proximal to the radially expansible region to allow blood to flow through the sleeve and to the catheter body orifices.

107. A method as in claim 105, wherein the radioactive element of the sleeve is evenly distributed around the circumference of the balloon when the balloon is inflated.

108. A method as in claim 105, further comprising fluoroscopically visualizing the catheter when aligning the balloon with the treatment region.

109. A method as in claim 105, wherein the radioactive element emits at least some beta radiation, and further comprising maintaining the catheter at the treatment region for a time in the range from about 1 min to about 20 min.

110. A catheter system comprising:
- a balloon catheter having a catheter body with a proximal end, a distal end, a lumen extending therebetween, and a balloon disposed near the distal end;
- a perfusion catheter having a radially deployable and contractible balloon containment region which defines an axial lumen and at least one perfusion lumen;
- at least one radioactive element distributed about the radially deployable region; and
- wherein the balloon catheter is insertable into the axial lumen of the perfusion catheter, wherein the balloon is expansible within the radially deployable region to move the radioactive element radially outward while allowing blood to flow past the inflated balloon through the perfusion lumen, and wherein the balloon containment region is contractible upon deflation of the balloon.

111. A catheter system as in claim 110, wherein the perfusion catheter includes orifices proximal and distal to the radially deployable region which are in communication with the perfusion lumen.

112. A catheter system as in claim 110, further comprising an elastomeric sleeve disposed over the radially deployable region of the perfusion catheter.

113. A catheter system as in claim 112, wherein the radioactive element is attached to an outer surface of the sleeve.

114. A catheter system as in claim 112, wherein the radioactive element is held between an inner surface of the sleeve and the perfusion catheter.

115. A catheter system comprising:
- an elongate housing which is folded into an expansible cage structure;
- at least one radioactive element disposed within the housing; and
- an elongate push rod having a proximal end and a distal end, wherein the distal end is operably attached to the housing, and wherein the push rod is sufficiently rigid to allow the rod to be pushed from the proximal end to move the distal end through a body lumen.

116. A catheter system as in claim 115, wherein the housing includes at least one necked region having a reduced cross sectional area to increase the transverse flexibility of the cage structure.

117. A catheter system as in claim 115, wherein the housing defines a plurality of folded regions where the housing is folded to form the cage structure, and wherein the folded regions have a reduced cross sectional area to facilitate expansion of the cage structure from a collapsed configuration to an expanded configuration.

118. A catheter system as in claim 115, further comprising a balloon catheter having a proximal end, a distal end, and a balloon near the distal end, wherein the cage structure is positionable over the balloon.

119. A method for providing radiation therapy to a patient, the method comprising:
- performing angioplasty on a body lumen to produce a treatment region;
- providing a catheter having a catheter body defining an inflation lumen and a balloon;
- placing an expansible cage structure over the balloon, the cage structure comprising a folded elongate housing and at least one radioactive element disposed within the housing, wherein an elongate push rod having a proximal end and a distal end is attached to the cage structure at the distal end;
- introducing the combined catheter and cage structure to the treatment region and inflating the balloon; and
- manipulating the proximal end of the push rod which is outside of the body lumen to manipulate the cage structure when within the body lumen.

120. A method as in claim 119, wherein the housing includes at least one necked region having a reduced cross sectional area to increase the transverse flexibility of the cage structure.

121. A method as in claim 119, wherein the housing defines a plurality of folded regions where the housing is folded to form the cage structure, and wherein the folded regions have a reduced cross sectional area to facilitate expansion and the cage structure from a collapsed configuration to an expanded configuration upon inflation of the balloon.

122. A catheter system, comprising:
- an elongate catheter body having a proximal end, a distal end;
- a head having an attachment mechanism for fixedly attaching the head to the distal end of the catheter body;
- at least one radioactive element operably attached to the head;
- an expansible member operably attached to the catheter body which radially expands the radioactive element away from a central axis of the catheter body; and
- a docking module defining an enclosure for housing the head, the docking module absorbing the release of radioactive energy from the radioactive element.

* * * * *